US011035797B2

(12) United States Patent
Yang et al.

(10) Patent No.: US 11,035,797 B2
(45) Date of Patent: Jun. 15, 2021

(54) HYBRID TIME-RESOLVED AND TIME-SHIFTED SPECTROSCOPY FOR MEASURING BIOLOGICAL ANALYTES

(71) Applicant: BioSpex, Inc., San Jose, CA (US)

(72) Inventors: Wei Yang, Los Altos, CA (US); Shu Zhang, Fremont, CA (US); Changqing Wang, Livermore, CA (US); Ming Chai, Union City, CA (US)

(73) Assignee: BioSpex, Inc., San Jose, CA (US)

( * ) Notice: Subject to any disclaimer, the term of this patent is extended or adjusted under 35 U.S.C. 154(b) by 0 days.

(21) Appl. No.: 16/718,120

(22) Filed: Dec. 17, 2019

(65) Prior Publication Data

US 2020/0124535 A1 Apr. 23, 2020

Related U.S. Application Data

(63) Continuation-in-part of application No. 15/847,876, filed on Dec. 19, 2017, now Pat. No. 10,876,892,
(Continued)

(51) Int. Cl.
*G01N 21/65* (2006.01)
*G01J 3/44* (2006.01)
(Continued)

(52) U.S. Cl.
CPC .............. *G01N 21/658* (2013.01); *G01J 3/44* (2013.01); *G01N 33/574* (2013.01); *G01N 33/66* (2013.01);
(Continued)

(58) Field of Classification Search
CPC ........... G01N 21/658; G01N 2021/655; G01N 33/66; G01N 33/92; G01N 33/574;
(Continued)

(56) References Cited

U.S. PATENT DOCUMENTS 5,615,673 A 4/1997 Berger et al.
6,665,556 B1 12/2003 Alfano et al.
(Continued)

OTHER PUBLICATIONS

Cooper, John B. et al., "Sequentially Shifted Excitation Raman Spectroscopy: Novel Algorithm and Instrumentation for Fluorescence-Free Raman Spectroscopy in Spectral Space", Society for Applied Spectroscopy, vol. 67, No. 8, 2013, pp. 973-984.
(Continued)

*Primary Examiner* — Eric F Winakur
*Assistant Examiner* — Abid A Mustansir
(74) *Attorney, Agent, or Firm* — Carr & Ferrell LLP

(57) ABSTRACT

Systems and methods for hybrid time-resolved and time-shifted spectroscopy for measuring biological analytes are disclosed. Exemplary methods include: illuminating an analyte using first light from and excitation source, the first light having a first excitation wavelength; detecting a first spectrum from the analyte illuminated by the first light using a time-resolved spectroscopy technique, the first spectrum including a first Raman signal and fluorescence; illuminating the analyte using second light, the second light having a second excitation wavelength; detecting a second spectrum using a time-resolved spectroscopy technique; illuminating the analyte using third light, the third light having a third excitation wavelength; detecting a third spectrum; recovering the first Raman signal using the first spectrum, the second spectrum, and the third spectrum using an inverse transform; and using the first Raman signal to identify and measure at least one molecule of the analyte using a database of identified Raman signals.

19 Claims, 15 Drawing Sheets

Related U.S. Application Data which is a continuation-in-part of application No. 15/582,428, filed on Apr. 28, 2017, now Pat. No. 10,548,481.

(51) Int. Cl.

| | |
|---|---|
| ***G01N 33/66*** | (2006.01) |
| ***G01N 33/92*** | (2006.01) |
| ***G01N 33/574*** | (2006.01) |

(52) U.S. Cl.

CPC ....... *G01N 33/92* (2013.01); *G01N 2021/655* (2013.01)

(58) Field of Classification Search

CPC .. G01N 21/65; G01J 3/44; G01J 3/108; G01J 2003/102; A61B 5/145; A61B 5/0075; A61B 5/0071

See application file for complete search history.

(56) References Cited

U.S. PATENT DOCUMENTS

| | | | |
|---|---|---|---|
| 8,072,595 | B1 | 12/2011 | Bastiaans et al. |
| 8,325,337 | B2 | 12/2012 | Sinfield et al. |
| 8,570,507 | B1 | 10/2013 | Cooper et al. |
| 8,873,041 | B1 | 10/2014 | Chai et al. |
| 9,554,738 | B1 | 1/2017 | Gulati et al. |
| 10,548,481 | B2 | 2/2020 | Yang et al. |
| 10,876,892 | B2 | 12/2020 | Yang et al. |
| 10,881,301 | B2 | 1/2021 | Periaki et al. |
| 2003/0059820 | A1 | 3/2003 | Vo-Dinh |
| 2007/0004975 | A1 | 1/2007 | Zribi et al. |
| 2007/0252978 | A1 | 11/2007 | Van Der Voort et al. |
| 2008/0129992 | A1 | 6/2008 | Matousek et al. |
| 2008/0198365 | A1 | 8/2008 | Treado et al. |
| 2011/0122407 | A1 | 5/2011 | Jalali et al. |
| 2012/0035442 | A1 | 2/2012 | Barman et al. |
| 2012/0287428 | A1 | 11/2012 | Tamada |
| 2013/0018237 | A1 | 1/2013 | Henneberg et al. |
| 2014/0268050 | A1 | 9/2014 | Jayaraman |
| 2016/0061660 | A1 | 3/2016 | Kim |
| 2018/0042527 | A1 | 2/2018 | Rawicz et al. |
| 2018/0299355 | A1 | 10/2018 | Young et al. |
| 2018/0310827 | A1 | 11/2018 | Yang et al. |
| 2018/0313692 | A1 | 11/2018 | Yang et al. |
| 2019/0128934 | A1 | 5/2019 | Park et al. |
| 2019/0154584 | A1 | 5/2019 | Ahn et al. |
| 2019/0274759 | A1 | 9/2019 | Royon |
| 2019/0370447 | A1 | 12/2019 | Houck et al. |
| 2020/0393299 | A1 | 12/2020 | Wang et al. |
| 2021/0010861 | A1 | 1/2021 | Yang et al. |
| 2021/0010865 | A1 | 1/2021 | Yang et al. |

OTHER PUBLICATIONS

Kostamovaara, J. et al., "Fluorescence suppression in Raman spectroscopy using a time-gated CMOS SPAD," Optics Express, Optics Society of America, vol. 21, No. 25, Dec. 13, 2013, 14 pages.

Nissinen, I. et al., "On the effects of the time gate position and width on the signal-to-noise ratio for detection of Raman spectrum in a time-gated CMOS single-photon avalanche diode based sensor," El Sevier, Sensors and Actuators B: Chemical, vol. 241, Mar. 31, 2017, pp. 1145-1152.

900

```
┌─────────────────────────────────────────────────┐
│        ILLUMINATE ANALYTE USING LIGHT           │
│  HAVING INITIAL EXCITATION WAVELENGTH AND/OR DURATION │
│                      910                        │
└─────────────────────────────────────────────────┘
                         ↓
┌─────────────────────────────────────────────────┐
│      DETECT SPECTRUM FROM ILLUMINATED ANALYTE   │
│                      920                        │
└─────────────────────────────────────────────────┘
                         ↓
┌─────────────────────────────────────────────────┐
│     INCREASE/DECREASE PRECEDING EXCITATION      │
│  WAVELENGTH BY PREDETERMINED INCREMENT/DECREMENT│
│                      930                        │
└─────────────────────────────────────────────────┘
                         ↓
┌─────────────────────────────────────────────────┐
│  ILLUMINATE ANALYTE USING LIGHT HAVING INCREASED/│
│       DECREASED EXCITATION WAVELENGTH           │
│                      940                        │
└─────────────────────────────────────────────────┘
                         ↓
┌─────────────────────────────────────────────────┐
│     DETECT SPECTRUM FROM ILLUMINATED ANALYTE    │
│                      950                        │
└─────────────────────────────────────────────────┘
                         ↓
                    ╱PRE-      ╲
              ╱DETERMINED NO. OF SPECTRA╲ — 960
         NO ╲       DETECTED?        ╱
                    ╲     ╱
                     YES
                      ↓
┌─────────────────────────────────────────────────┐
│          RECOVER SPECTRUM OF ANALYTE            │
│      USING PREDETERMINED NUMBER OF SPECTRA      │
│                      970                        │
└─────────────────────────────────────────────────┘
                         ↓
┌─────────────────────────────────────────────────┐
│   IDENTIFY MOLECULES USING RECOVERED SPECTRUM   │
│                  OF ANALYTE                     │
│                      980                        │
└─────────────────────────────────────────────────┘
```

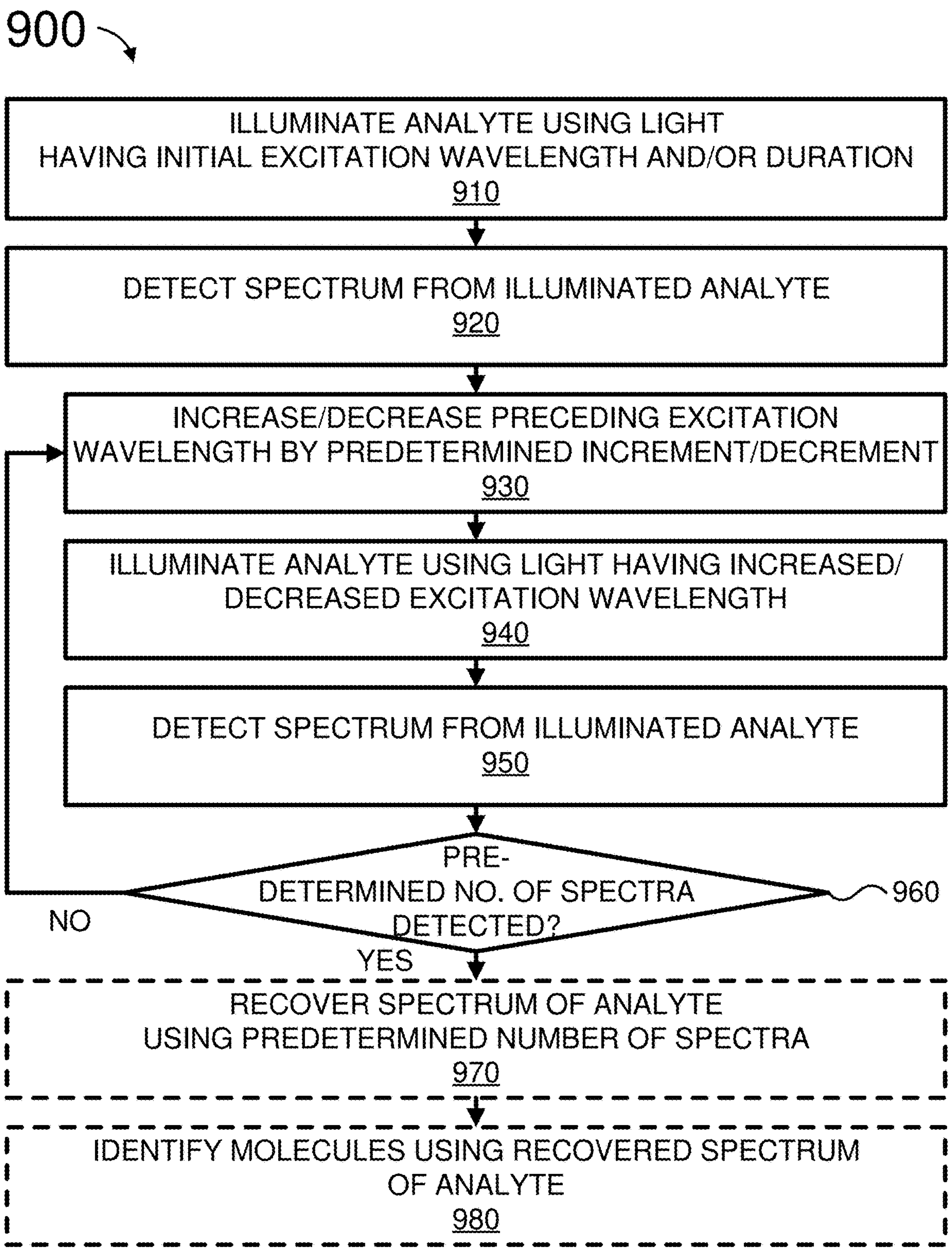

| MOLECULE | DIAGNOSTIC FOR |
|---|---|
| Carotenoid | Antioxidant levels |
| Glucose (HbA1c test) | Diabetes |
| Colon cancer biomarker (BM) | Cancer |
| Liver cancer BM | Cancer |
| Lung cancer BM | Cancer |
| Melanoma BM | Cancer |
| Stomach cancer BM | Cancer |
| HDL Cholestrol | Heart disease |
| LDL Cholestrol | Heart disease |
| Triglycerides | Heart disease |

FIG. 12

HYBRID TIME-RESOLVED AND TIME-SHIFTED SPECTROSCOPY FOR MEASURING BIOLOGICAL ANALYTES

CROSS REFERENCE TO RELATED APPLICATION

This application is a continuation-in-part of application Ser. No. 15/847,876, filed Dec. 19, 2017, which is a continuation-in-part of application Ser. No. 15/582,428, filed Apr. 28, 2017, the disclosures of which are incorporated by reference for all purposes.

TECHNICAL FIELD

The present technology relates generally to spectral imaging, and more specifically to measurement of biological analytes.

BACKGROUND

The approaches described in this section could be pursued but are not necessarily approaches that have previously been conceived or pursued. Therefore, unless otherwise indicated, it should not be assumed that any of the approaches described in this section qualify as prior art merely by virtue of their inclusion in this section.

Spectroscopy (or spectrography) refers to techniques that employ radiation in order to obtain data on the structure and properties of matter. Spectroscopy involves measuring and interpreting spectra that arise from the interaction of electromagnetic radiation (e.g., a form of energy propagated in the form of electromagnetic waves) with matter. Spectroscopy is concerned with the absorption, emission, or scattering of electromagnetic radiation by atoms or molecules.

Spectroscopy can include shining a beam of electromagnetic radiation onto a desired sample in order to observe how it responds to such stimulus. The response can be recorded as a function of radiation wavelength, and a plot of such responses can represent a spectrum. The energy of light (e.g., from low-energy radio waves to high-energy gammarays) can result in producing a spectrum.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

The present disclosure is related to various systems and methods for hybrid time-resolved and time-shifted spectroscopy. Specifically, a method for hybrid time-resolved and time-shifted spectroscopy for measuring biological analytes may comprise: illuminating an analyte using first light from an excitation source, the first light having a first excitation wavelength; detecting a first spectrum from the analyte illuminated by the first light using a time-resolved spectroscopy technique, the first spectrum including a first Raman signal and fluorescence; illuminating the analyte using second light from the excitation source, the second light having a second excitation wavelength, the second excitation wavelength being larger than the first excitation wavelength by a first predetermined increment; detecting a second spectrum from the analyte illuminated by the second light using a time-resolved spectroscopy technique, the second spectrum including a second Raman signal and the fluorescence, the detecting using a Raman spectrometer, the second Raman signal being shifted from the first Raman signal by a second predetermined increment; illuminating the analyte using third light from the excitation source, the third light having a third excitation wavelength, the third excitation wavelength being larger than the second excitation wavelength by the first predetermined increment; detecting a third spectrum from the analyte illuminated by the third light using a time-resolved spectroscopy technique, the third spectrum including a third Raman signal and the fluorescence, the third Raman signal being shifted from the second Raman signal by the second predetermined increment; recovering the first Raman signal using the first spectrum, the second spectrum, and the third spectrum using an inverse transform; and using the first Raman signal to identify and measure at least one molecule of the analyte using a database of identified Raman signals.

BRIEF DESCRIPTION OF THE DRAWINGS

Embodiments are illustrated by way of example, and not by limitation, in the figures of the accompanying drawings, in which like references indicate similar elements and in which:

FIG. 9 is a simplified flow diagram of a method for hybrid time-gated and time-resolved spectroscopy, according to some embodiments

FIG. 12 is a table of molecules, in accordance with various embodiments.

DETAILED DESCRIPTION

Figure 1:
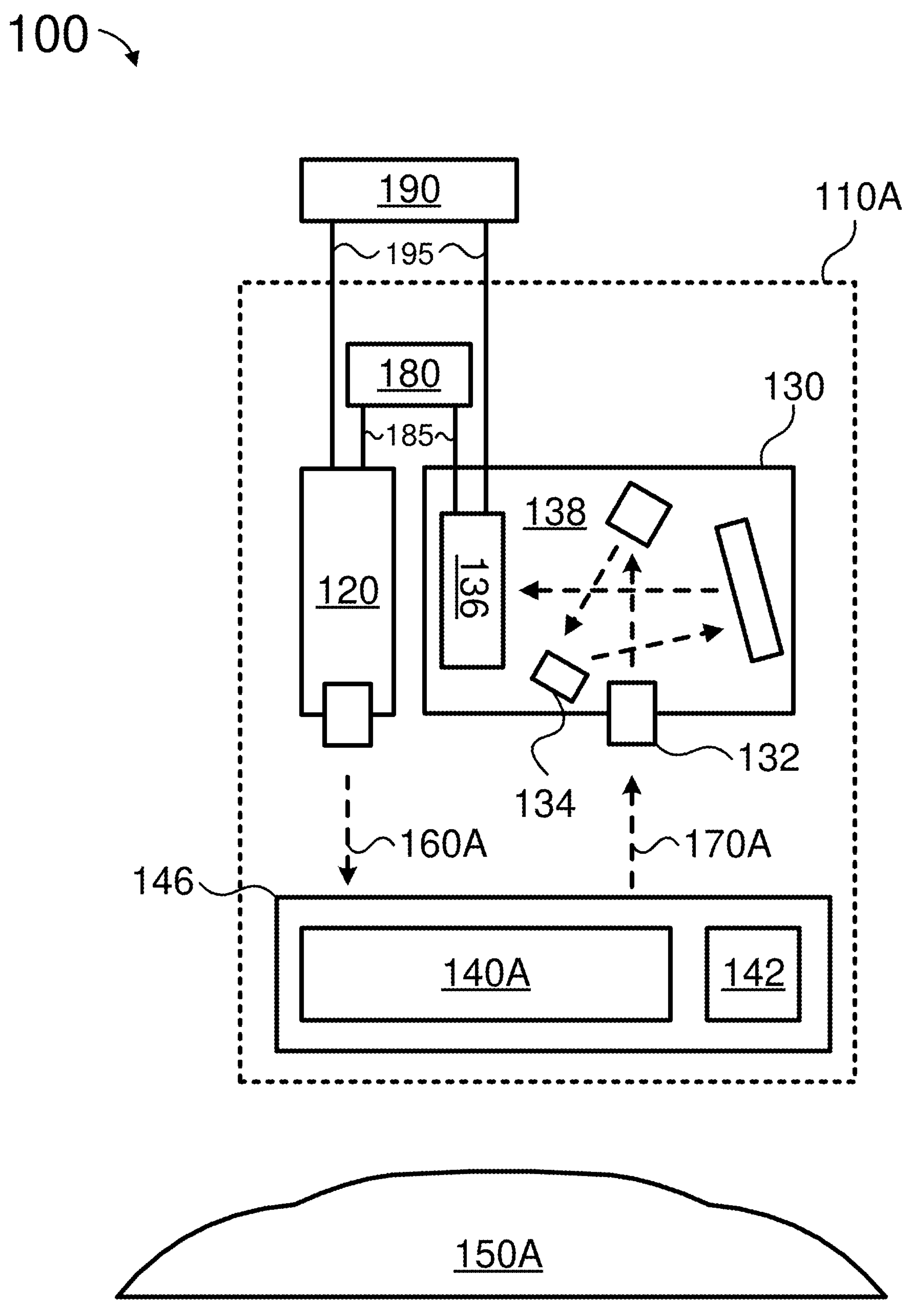
FIG. 1 is a simplified representation of a system for hybrid time-resolved and time-shifted spectroscopy for measuring biological analytes, according to some embodiments.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated. The terminology used herein is for the purpose of describing particular embodiments only and is not intended to be limiting of the technology. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

FIG. 1 illustrates system 100 for hybrid time-resolved and time-shifted spectroscopy for measuring biological analytes, according to some embodiments. System 100 can include spectrometer 110A, analyte 150A, and computing system 190.

According to some embodiments, analyte 150 is at least one of solid, liquid, plant tissue, human tissue, and animal tissue. For example, animal tissue is one or more of epithelial, nerve, connective, muscle, and vascular tissues. By way of further non-limiting example, plant tissue is one or more of meristematic (e.g., apical meristem and cambium), protective (e.g., epidermis and cork), fundamental (e.g., parenchyma, collenchyma and sclerenchyma), and vascular (e.g., xylem and phloem) tissues.

According to some embodiments, spectrometer 110A comprises excitation light source 120, optical bench 130, sampling apparatus 140A, stepper motor 142 for motion control, and delay 180. Excitation light source 120 is a monochromatic light source, such as a laser, in accordance with some embodiments. For example, excitation light source 120 is at least one of an Nd:YAG (neodymium-doped yttrium aluminium garnet; Nd:Y3Al5O12), Argon-ion, He—Ne, and diode laser. By way of further non-limiting example, excitation light source 120 can provide light (electromagnetic waves) in a range between ultra-violet (UV) light (e.g., electromagnetic radiation with a wavelength from 10 nm to 400 nm) and shortwave near-infrared (NIR) (1.4 μm to 3 μm), including portions of the electromagnetic spectrum in-between, such as visible light (e.g., 380 nm-760 nm) and NIR light (e.g., 0.75 μm to 1.4 μm).

In various embodiments, excitation light source 120 is tunable—a wavelength of the light from excitation light source 120 is changed by one or more (predetermined) increments and/or to one or more (predetermined) values—such as by using heat control (e.g., from a heating element), electrical control (e.g., using microelectromechanical systems (MEMS)), and mechanical control (e.g., using a mechanism to turn a mirror). Preferably, excitation light source 120 provides high spectral purity, high wavelength stability, and/or high power stability output.

Sampling apparatus 140A performs various combinations and permutations of directing light 160 from excitation light source 120, collecting the resulting Raman scattered light or Raman scatter (among others) 170, filtering out radiation at the wavelength corresponding to the laser line (e.g., Rayleigh scattering), and providing the Raman scatter (among others) 170 to optical bench 130, according to some embodiments. For example, sampling apparatus 140A includes a microscope and/or an optical probe. By way of further non-limiting example, sampling apparatus 140A includes optical fiber, one or more filters (e.g., notch filter, edge-pass filter, and band-pass filter), and the like. Raman scatter (among others) 170 includes, for example, at least one of Raman scatter, fluorescence, and Rayleigh scattering (which can be filtered out by sampling apparatus 140A).

Sampling apparatus 140A can be attached to or mounted on translation stage (or linear stage) 146. Translation stage 146 can restrict the motion of sampling apparatus 140A to a single axis of motion (or one degree of freedom out of six degrees of freedom). In various embodiments, translation stage 146 can include a (moving) platform and a (fixed) base (not depicted in FIG. 1), where the platform moves relative to the base. The platform and base can be joined by some form of guide which restricts motion of the platform to only one dimension. For example, guide types can be rollers, recirculating ball bearing, flexure, cylindrical sleeve, dovetail, and the like.

The position of the (moving) platform relative to the (fixed) base is typically controlled by a linear actuator. For example, a lead screw can pass through a lead nut in the platform. Rotation of the lead screw can be controlled by a motor, such as stepper motor 142. In this way, translation stage 146 can move sampling apparatus 140A (e.g., a probe) in spatial relationship to analyte 150A in a controlled manner.

Stepper motor 142 can move translation stage 146 to precisely change the distance between sampling apparatus 140A and analyte 150A in steps (increments) ranging from 2 μm to 0.5 nm. Stepper motor 142 can be a brushless DC electric motor that divides a full rotation into a number of equal steps. Stepper motor 142's rotational position can then be controlled (e.g., by computing system 190) to move and hold at one of these steps without needing a position sensor for feedback. Although translation stage 146 is shown including sampling apparatus 140A and stepper motor 142, in various embodiments translation stage 146 can include other constituent parts of spectrometer 110A and computing system 190.

In accordance with some embodiments, optical bench 130 is a spectrograph. For example, optical bench 130 includes slit 132, spectral dispersion element 134, and detector 136. By way of non-limiting example, optical bench 130 measures wavelengths in one or more of the UV spectrum (10 nm to 400 nm), visible spectrum (e.g., 380 nm-760 nm), visible to near-infrared (e.g., 400 nm-1000 nm), short-wave infrared (e.g., 950 nm-1700 nm), and infrared (e.g., 1 μm-5 μm).

Slit 132, spectral dispersion element 134, and detector 136 can be arranged in optical bench 138, along with other components (e.g., monochromator—which transmits a mechanically selectable narrow band of wavelengths of light or other radiation chosen from a wider range of wavelengths available at an input—including one or more of a mirror, prism, collimator, holographic grating, diffraction grating, blazed grating, and the like), according to different configurations. For example, different configurations include: crossed Czerny-Turner, unfolded Czerny-Turner, transmission, and concave holographic optical benches.

Slit 132 can determine the amount of light (e.g., photon flux, such as Raman scatter (among others) 170) that enters optical bench 138. Dimensions (e.g., height and width, not shown in FIG. 1) of slit 132 can determine the spectral resolution of optical bench 130. By way of non-limiting example, a height of slit 132 can range from 1 mm to 20 mm.

By way of further non-limiting example, a width of slit 132 can range from 5 μm to 800 μm.

Spectral dispersion element 134 can determine a wavelength range of optical bench 130 and can partially determine an optical resolution of optical bench 130. For example, spectral dispersion element 134 is a ruled diffraction grating or a holographic diffraction grating, in the form of a reflective or transmission package. Spectral dispersion element 134 can include a groove frequency and a blaze angle.

Detector 136 receives light and measures the intensity of scattered light. Detector 136 can be a one- or two-dimensional detector array comprised of a semiconductor material such as silicon (Si) and indium gallium arsenide (InGaAs). In some embodiments, a bandgap energy of the semiconductor determines an upper wavelength limit of detector 136. An array of detector 136 can be in different configurations, such as charged coupled devices (CCDs), back-thinned charge coupled devices (BT-CCDs), complementary metal-oxide-semiconductor (CMOS) devices, and photodiode arrays (PDAs). CCDs can be one or more of intensified CCDs (ICCDs) with photocathodes, back illuminated CCDs, and CCDs with light enhancing coatings (e.g., Lumogen® from BASF®). Detector 136 has a resolution of 8-15 wavenumbers, according to some embodiments. Detector 136 can be used to detect concentrations of molecules in a range of 1-1,000 mg per deciliter (mg/dL).

By way of further non-limiting example, detector 136 is a single pixel time-gated detector such as single-photon avalanche diode (SPAD), micro-channel plate (MCP), photomultiplier tube (PMT), silicon photomultiplier (SiPM), or avalanche photodiode (APD) that sits on a scanning motor driven rail, or detector arrays such as a single-photon avalanche diode (SPAD) array, or an intensified CCD (ICCD). A SPAD is a solid-state photodetector in which a photon-generated carrier (via the internal photoelectric effect) can trigger a short-duration but relatively large avalanche current. The leading edge of the avalanche pulse marks the arrival (time) of the detected photon. The avalanche current can continue until the avalanche is quenched (e.g., by lowering a bias voltage down to a breakdown voltage). According to various embodiments, each pixel in some SPAD arrays can count a single photon and the SPAD array can provide a digital output (e.g., a 1 or 0 to denote the presence or absence of a photon for each pixel).

To detect another photon, a control circuit(s) (not depicted in FIG. 1) integrated in and/or external to the SPAD can be used to read out measurements and quench the SPAD. For example, the control circuit can sense the leading edge of the avalanche current, generate a (standard) output pulse synchronous with the avalanche build up, quench the avalanche, and restore the diode to an operative level. The control circuit can provide passive quenching (e.g., passive quenching passive reset (PQPR), passive quench active reset (PQAR), and the like) and/or active quenching (e.g., active quench active reset (AQAR), active quenching passive reset (AQPR), and the like). In various embodiments, detector 136A is a complementary metal-oxide semiconductor (CMOS) SPAD array.

A micro-channel plate (MCP) is a planar component used for detection of single particles, such as photons. An MCP can intensify photons by the multiplication of electrons via secondary emission. Since a microchannel plate detector has many separate channels, it can also provide spatial resolution.

A photomultiplier tube (PMT) is a photoemissive device which can detect weak light signals. In a PMT, absorption of a photon results in the emission of an electron, where the electrons generated by a photocathode exposed to a photon flux are amplified. A PMT can acquire light through a glass or quartz window that covers a photosensitive surface, called a photocathode, which then releases electrons that are multiplied by electrodes known as metal channel dynodes. At the end of the dynode chain is an anode or collection electrode. Over a very large range, the current flowing from the anode to ground is directly proportional to the photoelectron flux generated by the photocathode.

Silicon photomultipliers (SiPM) are solid-state single-photon-sensitive devices based on Single-photon avalanche diode (SPAD) implemented on a common silicon substrate. Each SPAD in an SiPM can be coupled with the others by a metal or polysilicon quenching resistor.

Avalanche photodiodes (APDs) are semiconductor photodiodes with an internal gain mechanism. In an APD, absorption of incident photons creates electron-hole pairs. A high reverse bias voltage creates a strong internal electric field, which accelerates the electrons through the semiconductor crystal lattice and produces secondary electrons by impact ionization. The resulting electron avalanche can produce gain factors up to several hundred.

An intensified charge-coupled device (ICCD) is a CCD that is optically connected to an image intensifier that is mounted in front of the CCD. An image intensifier can include three functional elements: a photocathode, a micro-channel plate (MCP) and a phosphor screen. These three elements can be mounted one close behind the other. The photons which are coming from the light source fall onto the photocathode, thereby generating photoelectrons. The photoelectrons are accelerated towards the MCP by an electrical control voltage, applied between photocathode and MCP. The electrons are multiplied inside of the MCP and thereafter accelerated towards the phosphor screen. The phosphor screen converts the multiplied electrons back to photons which are guided to the CCD by a fiber optic or a lens. An image intensifier inherently includes shutter functionality. For example, when the control voltage between the photocathode and the MCP is reversed, the emitted photoelectrons are not accelerated towards the MCP but return to the photocathode. In this way, no electrons are multiplied and emitted by the MCP, no electrons are going to the phosphor screen, and no light is emitted from the image intensifier. In this case no light falls onto the CCD, which means that the shutter is closed.

Detector 136 can be other photodetectors having a time resolution of about one nanosecond or less. By way of further non-limiting example, detector 136 is a streak camera array, which can have a time-resolution of around 180 femtoseconds. A streak camera measures the variation in a pulse of light's intensity with time. A streak camera can transform the time variations of a light pulse into a spatial profile on a detector, by causing a time-varying deflection of the light across the width of the detector.

A spectral resolution of a spectrum measured by detector 136 can depend on the number of pixels (e.g., discrete photodetectors) in detector 136. A greater number of pixels can provide a higher spectral resolution. Detector 136 can comprise a one-dimensional and/or two-dimensional array of pixels. For example, detector 136 has in a range of 32 to 1,048,576 pixels. According to some embodiments, detector 136 has in a range of 512 to 1,024 pixels.

In some embodiments, the output (e.g., measurements) from detector 136 is provided to an analog-to-digital converter (ADC) (not shown in FIG. 1). The ADC can be integrated into detector 136 or separate from detector 136, such as in at least one of optical bench 130, spectrometer 110A, and computing system 190. The ADC can convert the measurements before the next measurements are received. For example, when measurements are received at 20 KHz, the ADC can convert at 20 KHz or faster. When the output of detector 136 is already a digital spectrum, analog-to-digital conversion is not needed.

Spectrometer 110A can provide information about molecular vibrations to identify and quantify characteristics (e.g., molecules) of analyte 150. Spectrometer 110A can direct light (electromagnetic waves) 160 from excitation light source 120 (optionally through sampling apparatus 140A) onto analyte 150. Light 160 from excitation light source 120 can be said to be shone on analyte 150 and/or analyte 150 can be said to be illuminated by excitation light source 120 and/or light 160. When (incident) light from excitation light source 120 hits analyte 150, the (incident) light scatters. A majority (e.g., 99.999999%) of the scattered light is the same frequency as the light from excitation light source 120 (e.g., Rayleigh or elastic scattering).

A small amount of the scattered light (e.g., on the order of $10^{-6}$ to $10^{-8}$ of the intensity of the (incident) light from excitation light source 120) is shifted in energy from the frequency of light 160 from excitation light source 120. The shift is due to interactions between (incident) light 160 from excitation light source 120 and the vibrational energy levels of molecules in analyte 150. (Incident) Light 160 interacts with molecular vibrations, phonons, or other excitations in analyte 150, causing the energy of the photons (of light 160 from excitation light source 120) to shift up or down (e.g., Raman or inelastic scattering). The shift in energy (e.g., of Raman scatter 170 from analyte 150) can be used to identify and quantify characteristics (e.g., molecules) of analyte 150.

Optical bench 130 detects (an intensity of) the Raman scatter 170 using detector 136 (optionally received through sampling apparatus 140A).

Spectrometer 110A can further include delay 180 for gating, according to some embodiments. Delay 180 can be communicatively coupled to excitation light source 120 and detector 136 through communications 185. In various embodiments, delay 180 can detect when excitation light source 120 provides light 160 (e.g., a laser pulse is emitted). For example, delay 180 can have a sensor (not depicted in FIG. 1) which detects light 160 being emitted from excitation light source 120. By way of further non-limiting example, excitation light source 120 can provide a (electronic) signal to delay 180 when excitation light source 120 provides light 160 (e.g., fires laser pulse). A predetermined amount of time after light 160 is detected/signaled, delay 180 can provide a signal indicating to detector 136 to (effectively) stop detecting and provide measurements (e.g., report a photon count at that time). The predetermined amount of time can be a gate. For example, the predetermined amount of time (e.g., gate or time window) can be selected using the duration of light 160 (e.g., a laser pulse), characteristics of the analyte being measured (e.g., duration/lifetime of fluorescence), and the like.

Delay 180 can be an (programmable) analog (e.g., continuous time) and/or digital (e.g., discrete time) delay line. In some embodiments, delay 180 is a network of electrical components connected in series, where each individual element creates a time difference between its input signal and its output signal. In various embodiments, delay 180 comprises one or more delay elements (e.g., forming a (circular) buffer) such as in discrete logic (e.g., flip flops, inverters, digital (or voltage) buffer, and the like), (general purpose) microprocessor, digital signal processor, application specific standard product (ASSP), application-specific integrated circuit (ASIC), field-programmable gate array (FPGA), and the like. Although depicted as a part of spectrometer 110A, delay 180 can alternatively be external to spectrometer 110A, such as part of computing system 190.

Spectrometer 110A can be communicatively coupled to computing system 190 through communications 195. Communications 195 can be various combinations and permutations of wired and wireless communications (e.g., networks) described below in relation to FIG. 9. Computing system 190 can include a database of Raman spectra associated with known molecules and/or remotely access the database over a communications network (not shown in FIG. 1). In some embodiments, computing system receives intensity measurements from spectrometer 110A, produces at least one Raman spectrum using data (e.g., intensity measurements) from spectrometer 110A, and identifies and/or quantifies molecules in analyte 150 using the at least one Raman spectrum and a database of Raman spectra associated with known molecules.

In some embodiments, computing system 190 is a single computing device. For example, computing system 190 is a desktop or notebook computer communicatively coupled to Spectrometer 110A through a Universal Serial Bus (USB) connection, a WiFi connection, and the like. In various embodiments, computing system 190 can be various combinations and permutations of stand-alone computers (e.g., smart phone, phablet, tablet computer, notebook computer, desktop computer, etc.) and resources in a cloud-based computing environment. For example, computing system 190 is a smart phone and a cloud-based computing system. The smart phone can receive data (e.g., intensity measurements) from spectrometer 110A using USB, Wi-Fi, Bluetooth, and the like. The smart phone can optionally produce at least one Raman spectrum using the data. The smart phone can transmit the data and/or at least one Raman spectrum to a cloud-based computing system over the Internet using a wireless network (e.g., cellular network). The cloud-based computing system can produce at least one Raman spectrum using the data and/or quantify and/or identify molecules in analyte 150 using the recovered Raman spectrograph. Although depicted as outside of spectrometer 110A, additionally or alternatively at least part of computing system 190 can be integrated into spectrometer 110A. Computing system 190 is described further in relation to FIG. 9.

According to some embodiments, spectrometer 110A offers at least some of the advantages of: differentiating chemical structures (even if they contain the same atoms in different arrangements), physical contact with analyte 150 not required, no damage to analyte 150 (e.g., non-destructive testing), preparation of analyte 150 is not required, analyte 150 can be in a transparent container (e.g., when light 160 is in the visible or near-visible light spectrum), sensitivity to small changes in material structure (e.g., detection of molecular vibrations is very sensitive to changes in chemistry and structure), analyzing samples in aqueous solutions (e.g., suspensions, biological samples, etc.), and the like.

Figure 2:
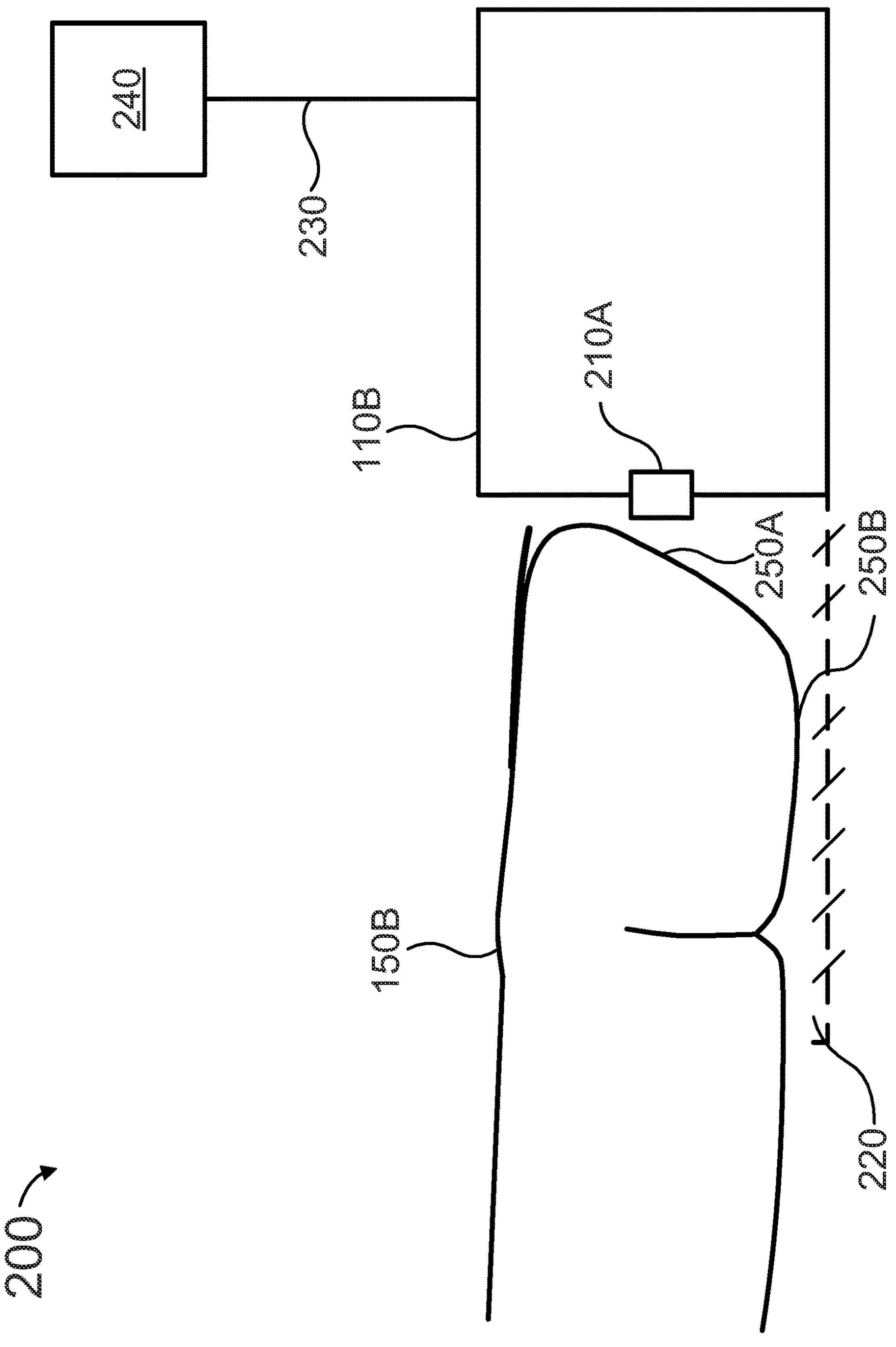
FIG. 2 is an alternate view of a system for spatial optimization for measuring biological analytes, according to various embodiments.

FIG. 2 is a simplified representation of system 200 of a system for hybrid time-resolved and time-shifted spectroscopy for measuring biological analytes, according to various embodiments. System 200 can be an alternative view of System 100 (FIG. 1). System 200 includes Raman instrument 110B and analyte 150B. Analyte 150B has at least some of the characteristics of analyte 150A (FIG. 1). Raman instrument 110E is depicted as being directed to a surface 250A of analyte 150B purely for illustrative purposes.

Raman instrument 110E can be oriented toward other surfaces of analyte 150B, such as surface 250B. Moreover, analyte 150B is depicted as a (human) finger purely for illustrative purposes. Other plant or animal tissue can be used. Alternatively or additionally, other parts of a human body (e.g., including a blood vessel, such as an earlobe, neck, face, back, chest, arm, leg, toe, and the like) may be used.

Raman instrument 110E has at least some of the characteristics of Raman instrument 110A (FIG. 1). Raman instrument 110E can include aperture 210A. Aperture 210A can be an opening through which light 160A from excitation light source 120 (FIG. 1) exits Raman instrument 110B and/or through which Raman scatter (among others) 170A enters Raman instrument 110B. For example, analyte 150B is illuminated by excitation light source 120 through aperture 210A and the Raman scatter (among others) 170A (FIG. 1) from analyte 150B is received by detector 130 (FIG. 1) through aperture 210A. Aperture 210A can include at least some of the features of optional sampling apparatus 140A (FIG. 1). Although aperture 210A is shown as one opening, aperture 210A can be more than one opening.

Raman instrument 110E can optionally include surface 220. In some embodiments, surface 220 is a surface on which analyte 150B is placed so that analyte 150B is positioned for measurement by Raman instrument 110E and/or analyte 150B does not substantially move during operation of Raman instrument 110E (e.g., substantial movement would cause a sample to change between measurements).

Raman instrument 110E can be a portable, handheld, or compact unit which can operate on battery power. Raman instrument 110E can be communicatively coupled to computing system 240 through communications 230. Communications 230 can be various combinations and permutations of wired and wireless communications (e.g., networks, busses, and the like) described below in relation to FIG. 10. Computing system 240 can include a database of Raman spectrographs associated with known molecules and/or remotely access the database over a communications network (not shown in FIG. 2). In some embodiments, computing system receives intensity measurements from Raman instrument 110B, produces at least one Raman spectrograph using data (e.g., intensity measurements) from Raman instrument 110B, and identifies and/or quantifies molecules in analyte 150B using the at least one Raman spectrograph and a database of Raman spectrographs associated with known molecules. Computing system 240 is described further below in relation to FIG. 10.

In some embodiments, computing system 240 is a single computing device. For example, computing system 240 is a desktop or notebook computer communicatively coupled to Raman instrument 110B through a Universal Serial Bus (USB) connection, a WiFi connection, and the like.

In various embodiments, computing system 240 is more than one (physical) computing device. For example, computing system 240 is a smart phone and a cloud-based computing system. The smart phone can receive data (e.g., intensity measurements) from Raman instrument 110E using USB, WiFi, Bluetooth, and the like. The smart phone can optionally produce at least one Raman spectrum (e.g., including the Raman signal and fluorescence, for each excitation wavelength) using the data. The smart phone can transmit the data and/or at least one Raman spectrum to a cloud-based computing system over the Internet using a wireless network (e.g., cellular network). The cloud-based computing system can produce at least one Raman spectrum using the data, recover a Raman spectrograph (e.g., without fluorescence) from the at least one received/produced Raman spectrum, and/or quantify and/or identify molecules in analyte 150B using the recovered Raman spectrograph.

By way of further non-limiting example, communications 230 and at least some of computing system 240 can be in a dock (or cradle or pad) (not depicted in FIG. 2) in (or on or adjacent to) which Raman instrument 110E is placed. When Raman instrument 110E is placed in (or on or adjacent to) the dock, communications 230 between Raman instrument 110E and computing system 240 can be various combinations and permutations of wired and/or wireless communications. Alternatively or additionally, the dock can charge a rechargeable battery (e.g., lithium ion battery) of Raman instrument 110E using wired and/or wireless charging. For example, the dock can include a connector (or plug or socket or other electrical contacts) which mates with a connector (or socket or plug or other electrical contacts) of Raman instrument 110E (not depicted in FIG. 2) for communications and/or charging. By way of further non-limiting example, the dock (and Raman instrument 110B) can include at least one antenna, coil, and the like for wireless communications and/or charging. Other combinations and permutations of communications 230 and computing system 240 (e.g., as described below in relation to FIG. 10) may be used.

Figure 3:
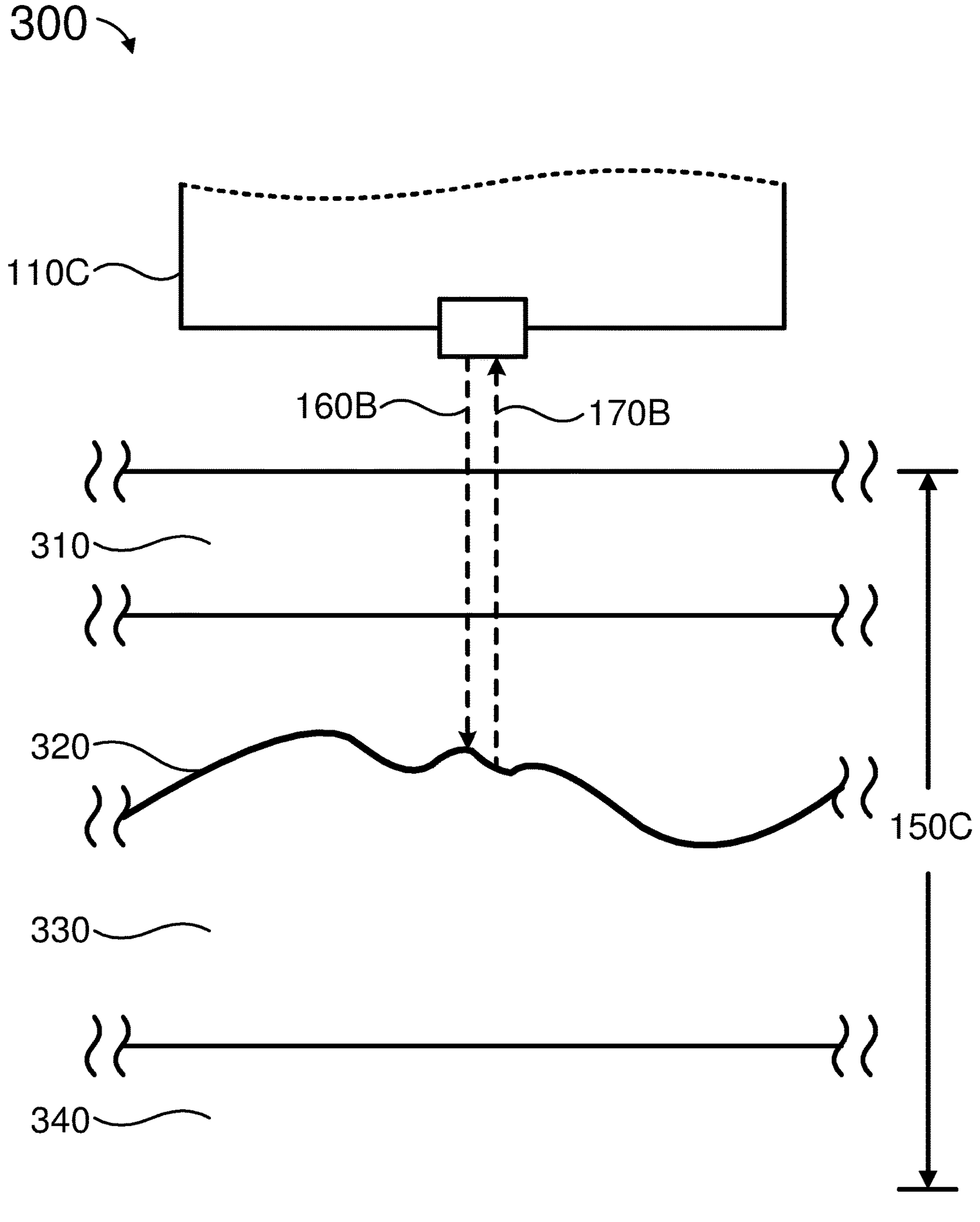
FIG. 3 is a cross-sectional view of the system of FIG. 2, in accordance with some embodiments.

FIG. 3 shows system 300, which is a simplified cross-sectional view of system 200 (FIG. 2) for hybrid time-resolved and time-shifted spectroscopy for measuring biological analytes, in accordance with some embodiments. System 300 includes spectrometer 110C and analyte 150C. Spectrometer 110C has at least some of the characteristics of spectrometer 110A (FIG. 1) and spectrometer 110B (FIG. 2). Analyte 150C has at least some of the characteristics of analyte 150A (FIG. 1) and analyte 150B (FIG. 2).

Analyte 150C can include layers, such as epidermis 310, dermis 330, and subcutaneous (fatty) tissue 340. Dermis 330 includes blood vessel 320 (e.g., vein and/or artery). For pictorial clarity, some features of epidermis 310, dermis 330, and subcutaneous (fatty) tissue 340 (e.g., hair shaft, sweat pore and duct, sensory nerve ending, sebaceous gland, pressure sensor, hair follicle, stratum, and the like) are not shown in FIG. 3.

Light 160B can have at least some of the characteristics of light 160A (FIG. 1). Light 160B (e.g., from excitation light source 120 (FIG. 1)) illuminates analyte 150C. Light 160B can pass through epidermis 310 to dermis 330. Photons of light 160B can bounce off molecules inside blood vessel 320. (Resulting) Raman scatter (among others) 170B is received by detector 130 (FIG. 1). Raman scatter (among others) 170B can have at least some of the characteristics of Raman scatter (among others) 170A (FIG. 1).

An optimal location for taking blood measurements is where the blood is, for example, blood vessel 320. Measurement accuracy can be compromised when light 160B overshoots or undershoots blood vessel 320. In human beings, blood vessel 320 is on the order of 80 μm thick and epidermis 310 is on the order of 200 μm, so it is easy to overshoot and/or undershoot blood vessel 320 (e.g., misses blood vessel 320). Spectrometer 110C can be precisely positioned relative to blood vessel 320, to ensure light 160B bounces off of blood vessel 320 and a quality measurement can be taken. The proper distance from spectrometer 110C to blood vessel 320 to ensure accurate blood measurement can vary, though. For example, the thickness of epidermis 310 can vary depending on where it is on the body. In addition, the thickness of epidermis 310 varies from person to person. Accordingly, embodiments of the present invention advantageously move sampling apparatus 140A to an optimal position for taking spectrographic measurements.

Details of analyte 150C, such as epidermis 310, dermis 330, and subcutaneous (fatty) tissue 340, are provided purely by way of example and not limitation. Analyte 150C can include other, more, and/or fewer details than those illustrated in FIG. 3. Analyte 150C is depicted as (human) tissue purely for illustrative purposes and other plant or animal tissue can be used.

Figure 4A:
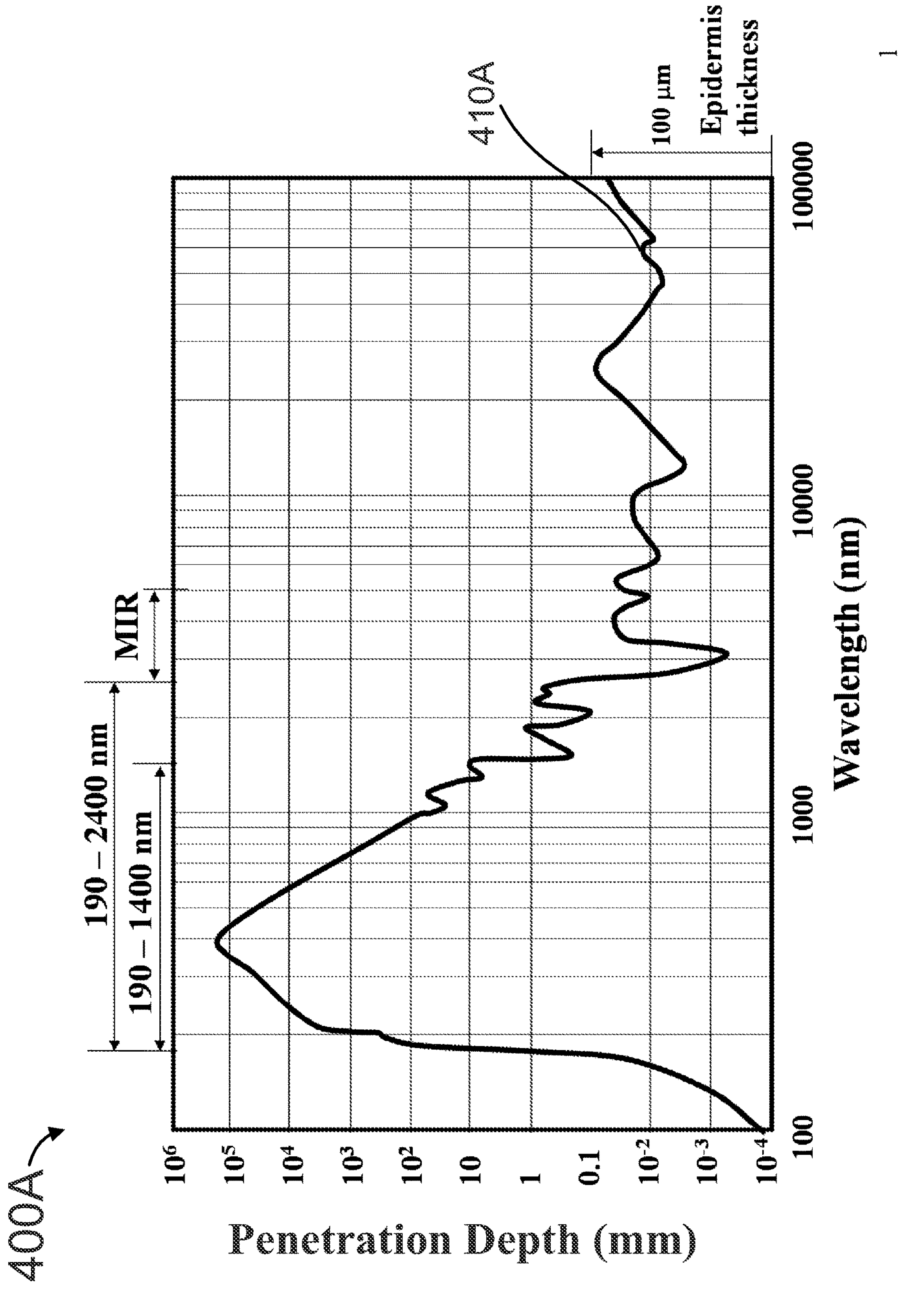
FIGS. 4A and 4B are graphical representations of penetration depth into liquid water and absorption spectra of biological tissues, respectively, in accordance with various embodiments.

FIG. 4A is a graphical representation (e.g., plot, graph, and the like) 400A of penetration depth 410A into liquid water of light over excitation wavelength. By way of non-limiting example, an epidermis (e.g., epidermis 310 in FIG. 3) can have a thickness on the order of 100 μm, so an excitation wavelength of light (e.g., light 160A and light 160B in FIGS. 1 and 3, respectfully) can be advantageously selected such that a penetration depth is at least 100 μm (e.g., approximately 190 nm to 2400 nm). In some embodiments, the excitation wavelength of light is in a range of 670 nm-900 nm for (human) tissue. Other ranges for the excitation wavelength of light can be used (e.g., depending on the depth of the tissue to be studied).

Figure 4B:
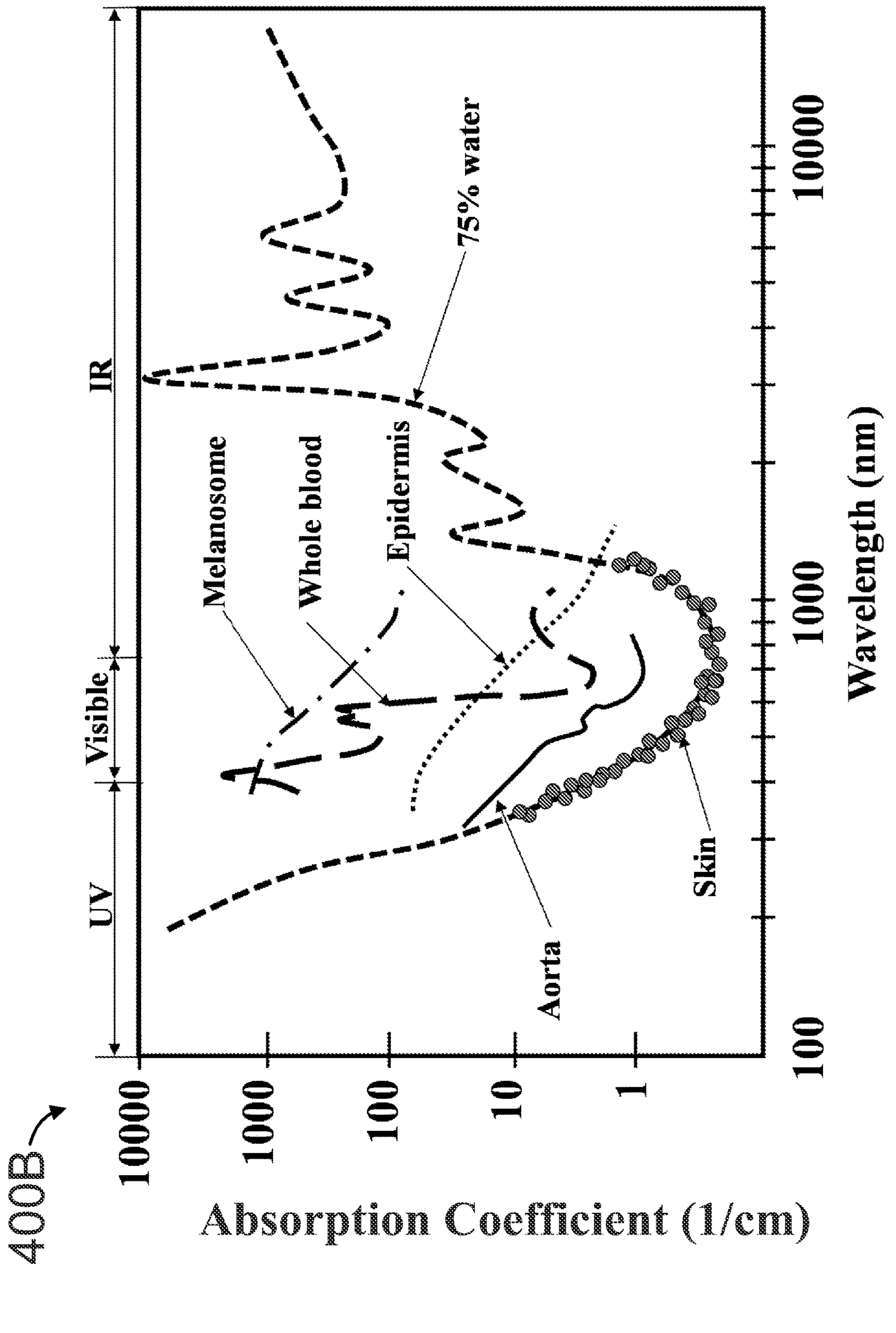

FIG. 4B is a graphical representation (e.g., plot, graph, and the like) 400B of absorption spectra of various tissues over excitation wavelength. By way of non-limiting example, an excitation wavelength of light (e.g., light 160A and light 160B in FIGS. 1 and 3, respectfully) can be advantageously selected to minimize the absorption coefficient so as to minimize absorption of the light by the tissue to be studied (e.g., so the light can scatter and be detected). When the tissue substantially absorbs light and/or Raman scatter (among others) (e.g., 170A and 170B in FIGS. 1 and 3, respectively), there can be insufficient Raman electromagnetic radiation for detector 130 to detect. For example, in skin tissue that has highly fluorescent chromophores, the increased absorption amplifies the emitted fluorescence and masks the weaker Raman signal. In various embodiments, the excitation wavelength of light is in a range of 670 nm-900 nm for (human) tissue. Other ranges for the excitation wavelength of light can be used (e.g., depending on the absorption coefficient of the tissue to be studied).

In embodiments where analyte (e.g., 150A-C (FIGS. 1-3)) is a live (and not dead) animal (e.g., living, alive, etc.), blood flows through blood vessel 320 (FIG. 3). Blood flow through blood vessel 320 in animals (e.g., humans) is caused by a heart (not shown in FIG. 4) pumping blood (e.g., beating heart). When measurements are taken at a rate slower than blood flows, different samples of blood are measured instead of the same sample and fluorescence will change with each sample.

When Raman instrument 110C takes multiple measurements, the measurements can be taken before the molecules in blood illuminated in one measurement (e.g., blood sample) flow away and are not available for the next measurement. For example, a resting adult human heart can beat at approximately 60 to 100 beats a minute (~1 Hz). Raman instrument 110C can take measurements within a tenth of a second (~0.1 KHz) or less, such that measurements are taken faster than blood flows (e.g., multiple measurements are taken from the same (instead of different) sample). Slower and/or faster sampling rates (e.g., frequency at which measurements are taken) can be used depending on the heart rate associated with analyte 150C (FIG. 3). In various embodiments, the sampling rate is 10 Hz-1 KHz.

Figure 5:
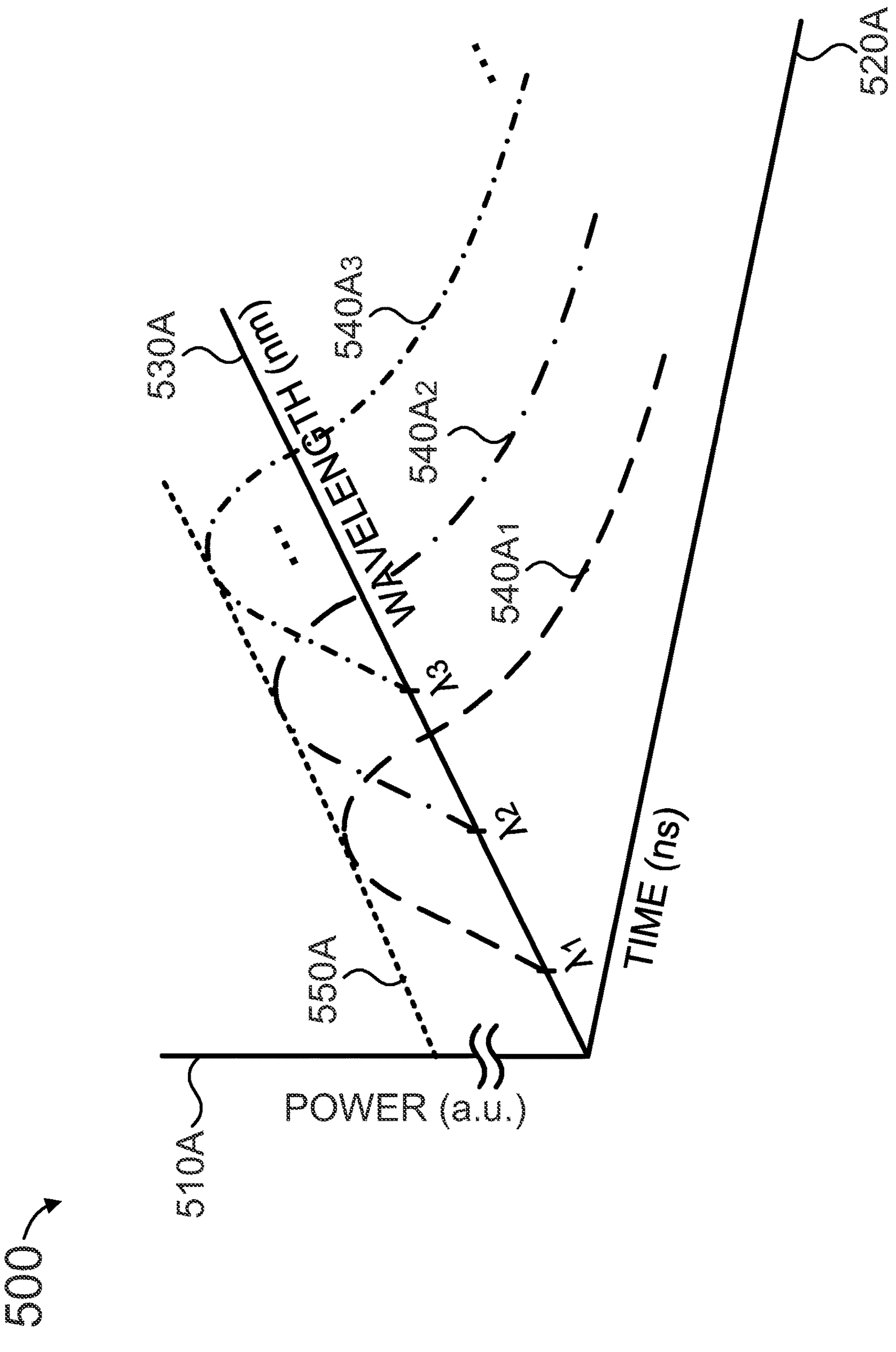
FIG. 5 is a simplified representation of spectra, according to some embodiments.

FIG. 5 illustrates example spectrum 500 produced using system 100 (FIG. 1), system 200 (FIG. 2), system 300 (FIG. 3), in some embodiments. A Raman spectrum—a plot/graph of an intensity of the Raman scattering (shifted light) against frequency—can be produced by a computing system 190 using intensity measurements from optical bench 130 (FIG. 1). Spectrum 500 (and 550A) can reliably be used to identify molecules in analyte 150A (FIG. 1), analyte 150B (FIG. 2), and analyte 150C (FIG. 3). In this way, Raman spectra (e.g., spectra 550A) can be said to produce a "fingerprint" of molecules in analyte 150. For example, Raman spectra (e.g., spectra 550A) of analyte 150 can be compared to a database (e.g., in the same or another computing system) of Raman spectra associated with known molecules to identify and quantify molecules in analyte 150A (FIG. 1), analyte 150B (FIG. 2), and analyte 150C (FIG. 3).

Spectrum 500 is plotted/graphed along three axes: intensity 510A, time 520A, and wavelength λ (or wavenumber) 530A. As shown in FIG. 5, intensity (axis 510A) can be power (light intensity) in a.u. (arbitrary units of intensity); other units can be milliwatts (mW) or photon count. Time (axis 520A) can be in nanoseconds (ns). Wavelength (axis 530A) can be a Raman shift in units such as nanometers (nm) or as a wavenumber in $cm^{-1}$. System 100 (FIG. 1), system 200 (FIG. 2), and system 300 (FIG. 3) can measure an intensity of Raman scatter having wavelength λ. For example, measurements taken at three wavelengths $\lambda_1$, $\lambda_2$, and $\lambda_3$ result in measurements 540$\lambda_1$, 540$\lambda_2$, and 540$\lambda_3$, respectively. Measurements 540$\lambda_1$, 540$\lambda_2$, and 540$\lambda_3$ show an intensity of Raman scattered light (the light having a particular wavelength $\lambda_1$, $\lambda_2$, and $\lambda_3$) over time. Measurements 540$\lambda_1$-540$\lambda_3$ can be collectively viewed when plotted/graphed along two axes: intensity 510A and wavelength λ (or wavenumber) 530A, which results in spectrum 550A (which can be referred to as a Raman spectrum). Spectrum 550A shows the peak intensity of Raman scatter at a range of wavelengths λ, such as wavelengths $\lambda_1$, $\lambda_2$, and $\lambda_3$ (or wavenumber).

Figure 6A:
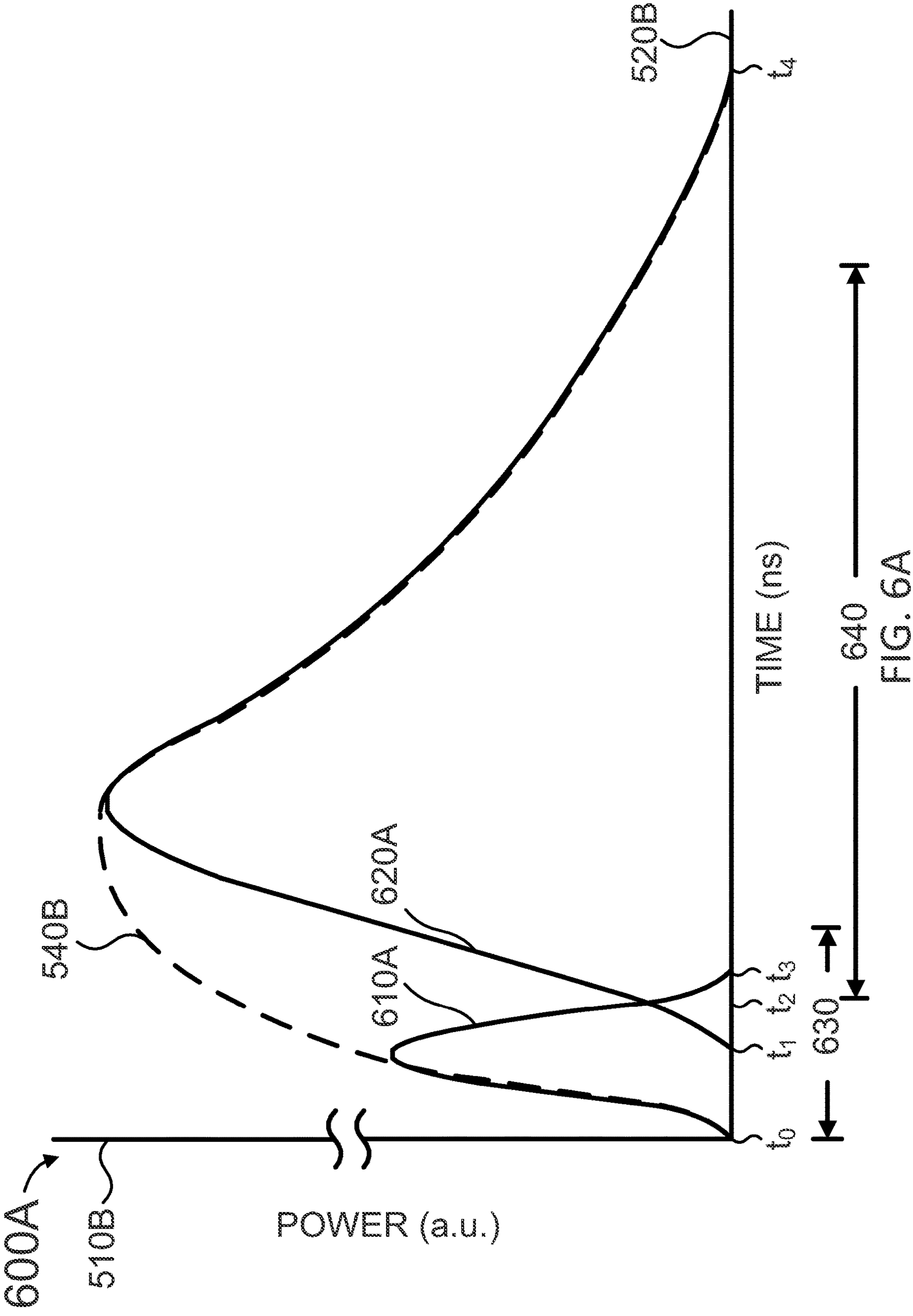
FIGS. 6A and 6B illustrate fluorescence, according to various embodiments

FIG. 6A shows graphical representation (e.g., plot, graph, and the like) 600A of (relative) (received) light intensity or power (e.g., in arbitrary units of intensity (a.u.), in milliwatts (mW), or photon count) along axis 510E over time (e.g., in nanoseconds) along axis 520B. Graphical representation 600A includes Raman signal 610A, fluorescence 620A, and total signal 540B, according to some embodiments. Raman signal 610A is, by way of non-limiting example, an intensity of a particular wavelength of Raman scatter for a material to be measured (e.g., analyte 150 in FIG. 1). Total signal 540B can have at least some of the characteristics of spectra 540$\lambda_1$-540$\lambda_3$ (FIG. 5) and be an intensity measured by a detector (e.g., optical bench 130 in FIG. 1) from (approximately) time $t_0$ to time $t_4$. In contrast to Raman scattering, fluorescence emission (fluorescence 620A) follows an absorption process. Fluorescence 620A can be several orders of magnitude (e.g., $10^5$-$10^6$) higher in intensity than Raman signal 610A and can overwhelm or obscure Raman signal 610A, such that Raman signal 610A is difficult to measure.

When light (e.g., light 160 in FIG. 1) from an excitation source (e.g., excitation light source 120 in FIG. 1) illuminates a material to be measured (e.g., analyte 150A (FIG. 1), analyte 150B (FIG. 2), and analyte 150C (FIG. 3)), receipt of the Raman signal (also called Raman scatter or return signal) 610A by a detector (e.g., detector 136 in FIG. 1) is almost instantaneous (e.g., ≤1 ps, depending on the distance travelled by the light and the Raman signal) (e.g., at time $t_0$). For this reason, Raman signal 610A can also be thought of as (approximately) representing the light from the excitation source, such as a laser pulse. In contrast, fluorescence 620A is received/occurs after Raman signal 610A (e.g., at time $t_1$).

When light from the excitation source illuminates the material to be measured (e.g., at time $t_0$), receipt of fluorescence 620A by the detector occurs later (e.g., at time $t_1$, which can be hundreds of nanoseconds or even milliseconds later).

When the detector (e.g., detector 136 in FIG. 1) is active (e.g., measuring light, detecting photons, and the like) while Raman signal 610A is present and before fluorescence 620A obscures/interferes with Raman signal 610A (e.g., from time $t_0$ to time $t_2$), Raman signal 610A can be measured by the detector without being completely overwhelmed or obscured by fluorescence 620A. Time window 630 is ideally narrow (relative to time window 640) and the time during which most (90%-100%) of the Raman photons are present and can be collected, although in practice time window 630 can be broader to include time when Raman photons are not present. For example, time window 630 is as wide (time-wise) as a laser pulse from excitation light source 120 (FIG. 1) (e.g., $t_0$-$t_3$). By way of further example, time window 630 is the time during which Raman signal 610A is present (e.g., approximately 80%-100% of peak intensity) and fluorescence 620A is mostly not present (e.g., from time $t_0$ to time $t_2$, time $t_0$ to time $t_3$, and the like) or is present.

As shown in FIG. 6A, although fluorescence 620A begins being received at time $t_1$, an intensity of fluorescence 620A may not be high enough to begin overwhelm or obscure Raman signal 610A until at or after time $t_2$. Control of the detector such that the detector is substantially active only during time window 630 can be referred to as gating. Moreover, time window 630 can also be referred to as gate 630. Gating can be used to reject a significant portion of fluorescence 620A.

In some embodiments, the detector (e.g., detector 136 in FIG. 1) is active (e.g., gate 630 in FIG. 6A) prior to the excitation source (e.g., excitation light source 120 in FIG. 1) providing light. By way of non-limiting example, (ideal) gate 630 is 1 ns (1,000 ps). The time resolution of the detector using the 1 ns (ideal) gate 630 is approximately equal to the laser pulse duration (e.g., 600 ps).

Time window 640 is a second time window or gate which is ideally broad/wide (relative to time window 630) and during which Raman photons are ideally not present and not detected, and fluorescence is present. In practice, Raman photons may be present during time window 640. For example, during time window 640, little of Raman signal 610A is present (e.g., 0%-20% of peak intensity).

As shown in FIG. 6A, time window 640 can partially (or completely) overlap with time window 630. Alternatively, time window 630 and time window 640 can be contiguous. In other words, time window 630 and time window 640 occur one after the other sequentially. For example, time window 640 can begin (almost immediately) after time window 630 ends, and can end before the intensity of total signal 540B drops to zero (e.g., at time $t_4$). For example, time window 640 can extend out to time $t_4$. In various embodiments, time window 630 ends and time window 640 begins before or after $t_1$ (or $t_2$). Generally, time window 630 is shorter in duration than time window 640, although time window 630 can be greater-than-or-equal-to time window 640.

The spectrometer (e.g., spectrometer 110A (FIG. 1), spectrometer 110E (FIG. 2), and spectrometer 110C (FIG. 3)) can be controlled such that measurements can be taken during both time window 630 and time window 640 using one pulse (e.g., of light from excitation light source 120). Alternatively or additionally, two pulses (e.g., of light from excitation light source 120), one pulse for measurements in time window 630 and another pulse during time window 640.

Figure 6B:
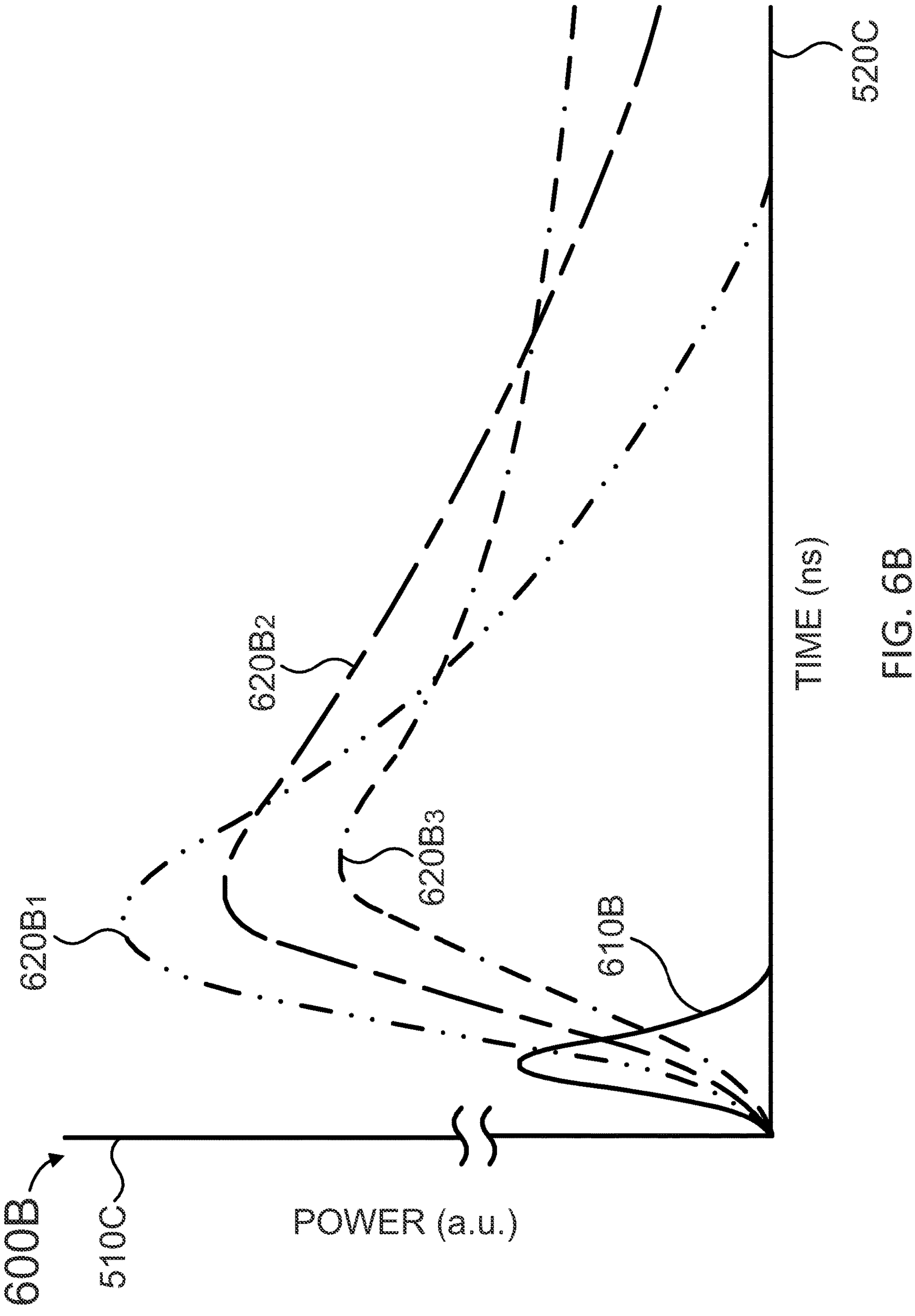

FIG. 6B depicts graphical representation (e.g., plot, graph, and the like) 600B of (relative) (received) light intensity or power (e.g., in arbitrary units of intensity (a.u.), in milliwatts (mW), or photon count) (along axis 510C) over time (e.g., in nanoseconds) along axis 520C from a (e.g., 600 ps) laser pulse, in accordance with some embodiments. Graphical representation 600B can include Raman signal 610B and fluorescence 620$B_1$-620$B_3$. Graphical representation 600B can show relative intensities and/or lifetimes/durations of Raman signal 610B and fluorescence 620$B_1$-620$B_3$. Raman signal 610B has at least some of the characteristics of Raman signal 610A described above in relation to FIG. 6A. Fluorescence 620$B_1$-620$B_3$ can have at least some of the characteristics of fluorescence 620A (FIG. 6A). Since Raman scattering occurs almost immediately (e.g., ≤1 ps, depending on the distance travelled by the light and the Raman signal) after an excitation light pulse from the excitation source (e.g., excitation light source 120 in FIG. 1), Raman signal 610B can also (approximately) represent the excitation light pulse.

Graphical representation 600B illustrates the relative intensities and/or the relative lifetimes/durations among fluorescence 620$B_1$-620$B_3$, according to various embodiments. Raman signal 610B can have at least some of the characteristics of Raman signal 610A (FIG. 3A). Fluorescence 620$B_1$-620$B_3$ can have at least some of the characteristics of fluorescence 620A (FIG. 6A). In some embodiments, fluorescence 620$B_1$-620$B_3$ results when light (e.g., light 160 in FIG. 1) from an excitation source (e.g., excitation light source 120 in FIG. 1) illuminates a material to be measured (e.g., analyte 150A (FIG. 1), analyte 150B (FIG. 2), and analyte 150C (FIG. 3)), where the wavelength of the light used varies. In other words, fluorescence 620$B_1$-620$B_3$ can be from the same material, but the wavelength of the light used is different.

As shown in FIG. 6B, each of fluorescence 620$B_1$-620$B_3$ can have a different lifetime/duration, with fluorescence 620$B_1$ having the shortest and fluorescence 620$B_3$ having the longest. By way of non-limiting example, fluorescence 320$B_1$ has a 1 ns lifetime/duration, fluorescence 320$B_2$ has a 5 ns lifetime/duration, and fluorescence 320$B_3$ has a 10 ns lifetime/duration. Depending upon the material, a fluorescence can have other lifetimes/durations (e.g., 100 ps-10 ms). As shown in FIG. 6B, the longer the lifetime/duration of a respective one of fluorescence 620$B_1$-620$B_3$, the lower the intensity of a respective one of fluorescence 620$B_1$-620B3 can be. Moreover, the decay rate of fluorescence 620$B_1$-620$B_3$ is different at each frequency.

Figure 7:
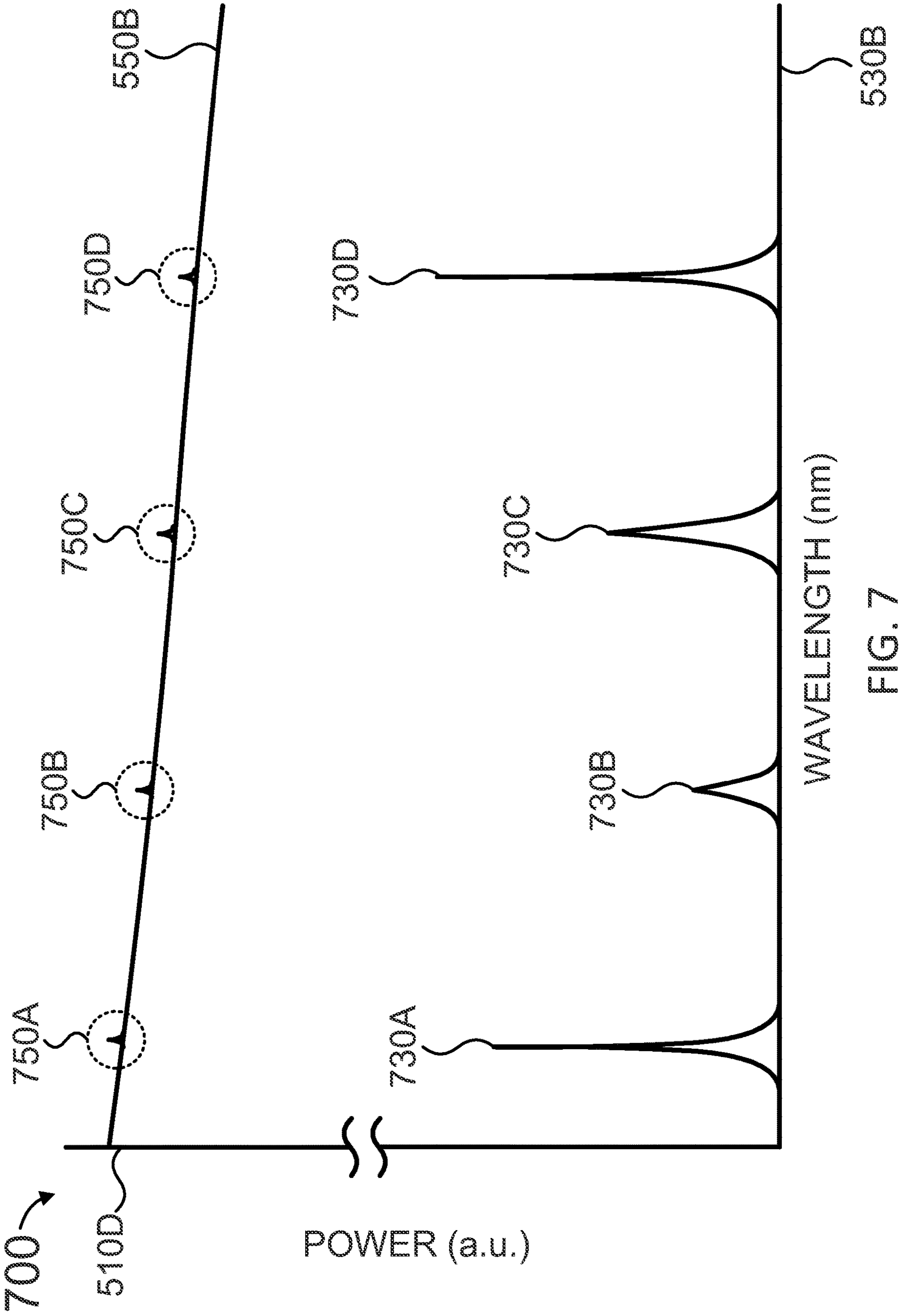
FIG. 7 is a simplified graphical representation of intensity, in accordance with some embodiments.

FIG. 7 illustrates graphical representation (e.g., plot, graph, and the like) 700 of (relative) (received) light intensity or power (e.g., in arbitrary units of intensity (a.u.), in milliwatts (mW), or photon count) along axis 510D over received light wavelength (e.g., in nanometers (nm)) along axis 530B. Graphical representation 700 includes Raman signal 730 (730A-730D). Raman signal 730 can be obscured by fluorescence (e.g., fluorescence 620A (FIG. 6A) and fluorescence 620$B_1$-620$B_3$ (FIG. 6B)), resulting in spectrum 550B. Raman signal 730 is a Raman spectrograph for an analyte (e.g., analyte 150A-C (FIGS. 1-3) that would be measured if it were not overwhelmed/obscured by fluorescence. Although Raman signal 730 is shown having four peaks at regular intervals, Raman signal 730 may have any number of peaks having different intensities and occurring at different/irregular frequencies. The peaks of Raman signal 730 can indicate information about different molecular bonds.

When light (e.g., light 160A and 160B in FIGS. 1 and 3, respectively) illuminates analyte (e.g., analyte 150A-C in FIGS. 1-3, respectively), fluorescence (e.g., fluorescence 620A (FIG. 6A) and fluorescence 620$B_1$-620$B_3$ (FIG. 6B)) (in addition to Raman signal 530 (530A-530D)) can result. Fluorescence can be several orders of magnitude (e.g. $10^5$-$10^6$) higher in intensity than Raman signal 730. Fluorescence can overwhelm or obscure Raman signal 730, such that Raman signal 730 is difficult to actually measure.

An intensity measured by detector 130 (FIG. 1) includes an intensity (I) of the Raman signal ($I_R$) and intensity of fluorescence ($I_F$) at each wavelength (e.g., $I=I_R+I_F$). For example, the intensity measured by detector 130 (FIG. 1) would look like fluorescence (e.g., fluorescence 620A (FIG. 6A) and fluorescence 620$B_1$-620$B_3$ (FIG. 6B)) with very small contributions 750A-750D from Raman signal 530 (530A-530D), resulting in spectrum 550B. Contributions 750A-750D are provided for illustrative purposes and are not drawn to scale. Fluorescence is several orders of magnitude (e.g. $10^5$-$10^6$) larger than Raman signal 730 and contributions 750A-750D may not be visible if shown to scale.

An intensity of the Raman signal is inversely proportional to the excitation wavelength (λ) of light (e.g., light 160A and 160B in FIGS. 1 and 3, respectively) (e.g., Raman signal strength $\alpha\ \lambda^{-4}$). In contrast, an intensity of the fluorescence is proportional to the excitation wavelength (λ). Generally, when a longer excitation wavelength (λ) is used to illuminate tissue, there is less fluorescence but the Raman signal strength becomes smaller and difficult to measure. Likewise, when a shorter excitation wavelength (λ) is used (e.g., in the near infrared (NR) spectrum) to illuminate tissue, too much fluorescence is produced making it difficult to measure the Raman signal.

Figure 8:
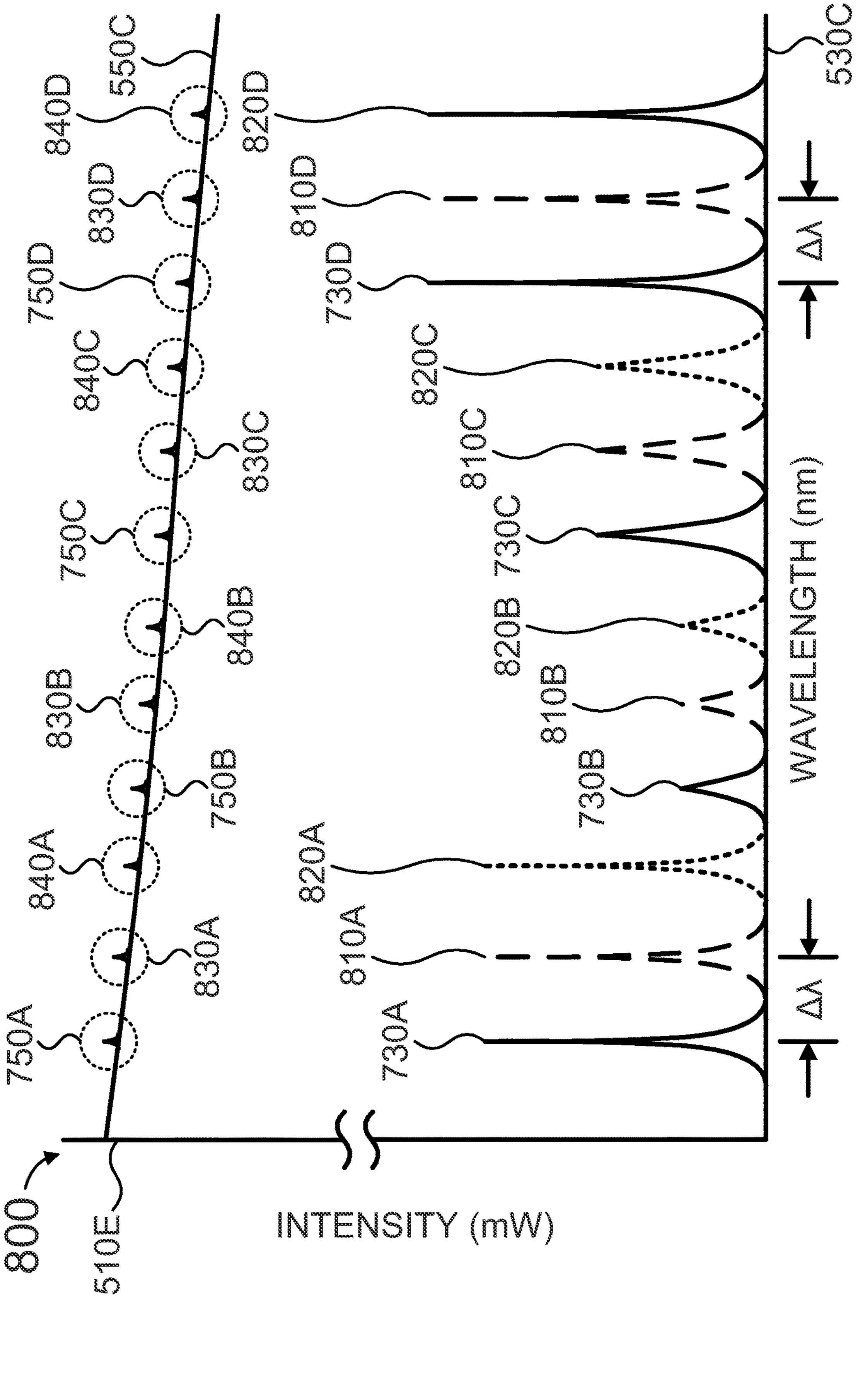
FIG. 8 is a simplified graphical representation of intensity for more than one excitation wavelength, in accordance with various embodiments.

FIG. 8 depicts graphical representation (e.g., plot, graph, and the like) 800 of (relative) (received) light intensity or power (e.g., in arbitrary units of intensity (a.u.), in milliwatts (mW), or photon count) along axis 510E over received light wavelength (e.g., in nanometers (nm)) along axis 530C, according to some embodiments. Graphical representation 800 includes Raman signal 730 (730A-730D), Raman signal 810 (810A-810D), Raman signal 820 (820A-820D), and spectrum 550C. Raman signal 730 was described above in relation to FIG. 7. Raman signals 810 and 820 are Raman spectrographs for analyte (e.g., analyte 150A-C in FIGS. 1-3, respectively) that would be measured if it were not overwhelmed/obscured by fluorescence (e.g., fluorescence 620A (FIG. 6A) and fluorescence 620$B_1$-620$B_3$ (FIG. 6B)). Although Raman signals 810 and 820 are shown each having four peaks at regular intervals, Raman signals 810 and 820 may have any number of peaks having different intensities and occurring at different/irregular frequencies (e.g., corresponding to or following Raman signal 730). Raman signals 730, 810, and 820 can result from different excitation wavelengths (λ).

As described above, excitation light source 120 (FIG. 1) can be tunable, such that an excitation wavelength can change (e.g., by a predetermined increment, to one or more predetermined wavelengths, etc.). When measurements are (sequentially) taken at different excitation wavelengths (λ) (e.g., $\lambda=\lambda_0, \lambda_1, \lambda_2, \ldots$), a Raman signal for each excitation wavelength can be produced. For example, Raman signal 730 (730A-730D) is measured at $\lambda=\lambda_0$, Raman signal 810 (810A-810D) at $\lambda=\lambda_1$, and Raman signal 820 (820A-820D) $\lambda=\lambda_2$. Although three different excitation wavelengths (e.g., $\lambda=\lambda_0, \lambda_1, \lambda_2$) are used, any number N of different excitation wavelengths can be used (e.g., $\lambda=\lambda_0, \lambda_1, \ldots \lambda_N$). N can be a function of a sampling rate of Raman instrument (e.g., Raman instrument 110A (FIG. 1), 110E (FIG. 2), and 110C (FIG. 3)), a molecule to be detected and/or quantified, and the like. The excitation wavelength can be incremented/decremented by a predetermined amount Δλ, such that $\lambda_1=\lambda_0+\Delta\lambda$, $\lambda_2=\lambda_1+\Delta\lambda$, $\lambda_3=\lambda_2+\Delta\lambda$, etc. As shown in FIG. 8, Raman signals 810 and 820 can be shifted from an adjacent Raman signal (e.g., Raman signals 730 and 810, respectively) by Δλ. Although Raman signals 730, 810, and 820 are shifted (e.g., by Δλ), the envelopes (e.g., amplitude and frequency of the peaks) of Raman signals 730, 810, and 820 are consistent. At each of $\lambda=\lambda_0, \lambda_1, \lambda_2, \ldots$, fluorescence (e.g., fluorescence 620A (FIG. 6A) and fluorescence 620$B_1$-620$B_3$ (FIG. 6B)) remains the same (e.g., as long as the analyte (e.g., analyte 150A (FIG. 1), analyte 150B (FIG. 2), and analyte 150C (FIG. 3)), (blood) sample, and the like does not change (enough to change the spectrum)).

An intensity measured by detector 130 (FIG. 1) includes an intensity (I) of the Raman signal ($I_R$) and intensity of fluorescence ($I_F$) at each wavelength (e.g., $I=I_R+I_F$), as described above in relation to FIG. 7. For example, for excitation wavelength $\lambda=\lambda_1$, spectrum 550C would look like fluorescence (e.g., fluorescence 620A (FIG. 6A) and fluorescence 620$B_1$-620$B_3$ (FIG. 6B)) with very small contributions (e.g., contributions 830A-830D) from Raman signal 810 (810A-810D). By way of further non-limiting example, for excitation wavelength $\lambda=\lambda_2$, spectrum 550C would look like fluorescence with very small contributions (e.g., 840A-840D) from Raman signal 820 (820A-820D). Contributions 830A-D and 840A-D are provided for illustrative purposes and are not drawn to scale.

As described below in relation to FIGS. 9-11, a Raman spectrograph for analyte (e.g., analyte 150A (FIG. 1), analyte 150B (FIG. 2), and analyte 150C (FIG. 3) (e.g., compensating for fluorescence) can be produced using Raman signals 730 (730A-730D), 810 (810A-810D), 820 (820A-820D), etc.

Figure 13:
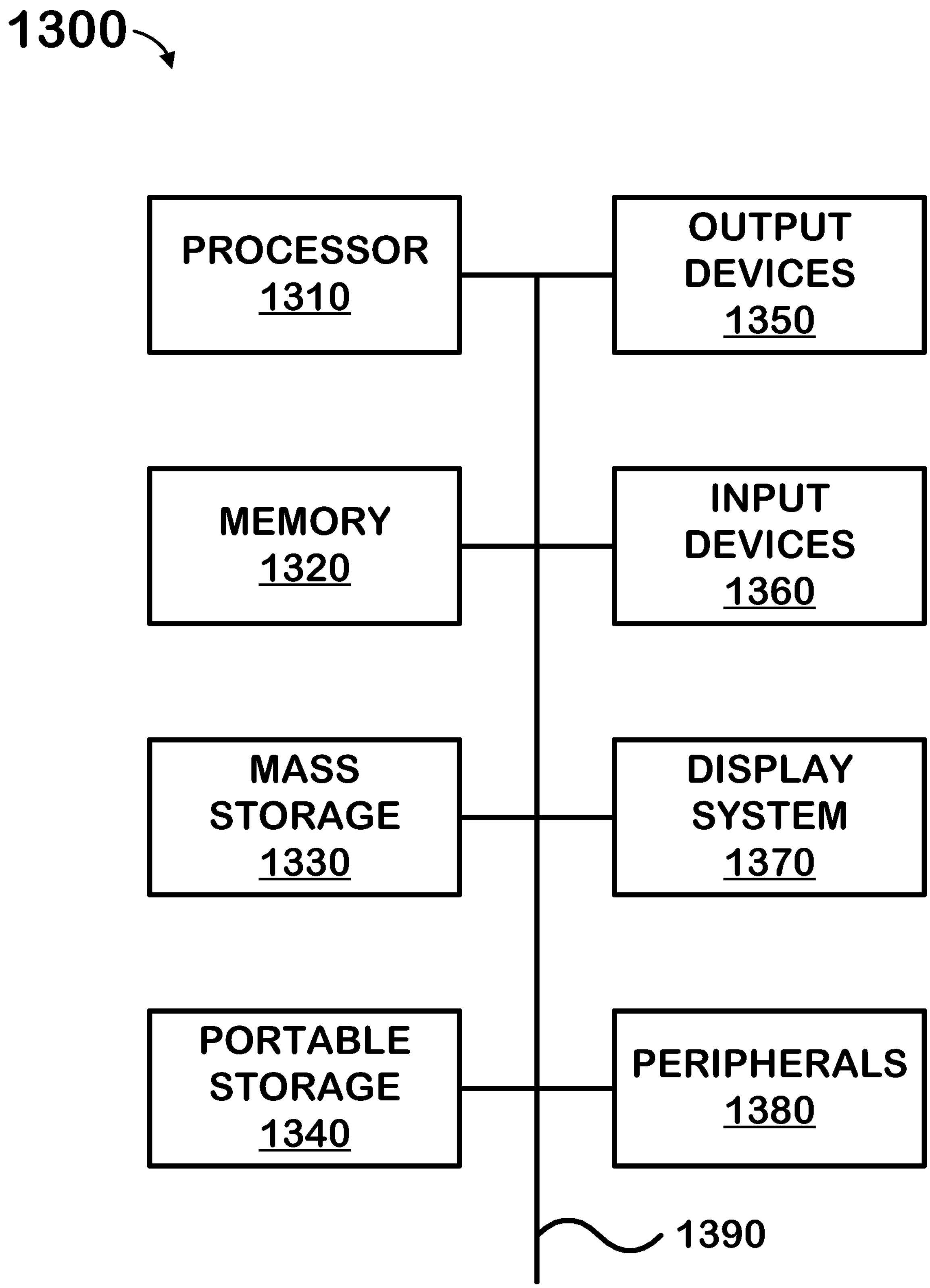
FIG. 13 is a simplified block diagram of a computing system, according to some embodiments.

FIG. 9 illustrates method 900 for hybrid time-resolved and time-shifted spectroscopy of biological analytes, according to some embodiments. Method 900 can be performed by a Raman instrument and/or a computing system. The Raman instrument can have at least some of the characteristics of Raman instrument 110A (FIG. 1), Raman instrument 110E (FIG. 2), and Raman instrument 110C (FIG. 3). The computing system can have at least some of the characteristics of computing system 240 (FIG. 2) and computing system 1300 (FIG. 13).

Method 900 can commence at step 910, where an analyte can be illuminated using light having an initial excitation wavelength. For example, the analyte has at least some of the characteristics of analyte 150A (FIG. 1), analyte 150B (FIG. 2), and analyte 150C (FIG. 3). By way of further non-limiting example, the light can be provided by the Raman instrument, for example, using excitation light source 120 (FIG. 1). For illustrative purposes, the initial excitation wavelength can referred to as $\lambda_0$ and can have a value of 670 nm (e.g., $\lambda_0$=670 nm). Other values for $\lambda_0$ can be used.

In some embodiments, the provided light has a predetermined wavelength and/or duration. For example, the predetermined wavelength (also called an excitation wavelength) can depend on the material to be measured and be selected to minimize absorption (by the material) of the provided light and maximize the Raman signal, such as described above in relation to FIGS. 6A-6B. In addition, a shorter excitation wavelength can provide a stronger Raman signal than a longer excitation wavelength. In some embodiments, the excitation wavelength is in a range of 450 nm-650 nm.

By way of further non-limiting example, the predetermined duration can be selected so as to at least provide a Raman signal of sufficient duration to be measured by detector 136, such as the gate (e.g., time window 630 in FIG. 6A). At or after the receipt or occurrence of fluorescence, the provided light is not needed and may stop. In various embodiments, the predetermined duration is in a range of 200 ps-2 ns. For example, the predetermined duration is on the order of 600 ps.

At step 920, a spectrum (e.g., including Raman scattering (or Raman signal) and fluorescence) can be detected from the illuminated analyte. In some embodiments, the light hitting the analyte results in Raman scattering (or Raman signal) and fluorescence. For example, the Raman scattering (e.g., contributions 750A-D, 830A-D, and 840A-D) and fluorescence can be detected by the Raman instrument (e.g., using detector 130 optionally through optional sampling apparatus 140A (FIG. 1)). By way of further non-limiting example, the detected Raman scattering (e.g., contributions 750A-D) and fluorescence may appear (e.g., when graphed, plotted, and the like) as shown in spectrum 550B (where the excitation wavelength is $\lambda_0$). The detected spectrum (e.g., data, graphical representation, and the like) can be stored in the Raman instrument and/or the computing system.

According to various embodiments, the spectrum can be detected at step 920 using a time-resolving technique described below in relation to FIG. 10.

At step 930, the preceding excitation wavelength can be increased or decreased by a predetermined increment or decrement, respectively. For illustrative purposes, the predetermined increment/decrement can be referred to as $\Delta\lambda$. For example, when the preceding excitation wavelength is $\lambda_0$, an increased/decreased excitation wavelength is $\lambda_1$, where $\lambda_1=\lambda_0+\Delta\lambda$. By way of further non-limiting example, when the preceding excitation wavelength is $\lambda_1$, an increased/decreased excitation wavelength is $\lambda_2$, where $\lambda_2=\lambda_1+\Delta\lambda$. By way of additional non-limiting example, when N spectra are to be detected, $\lambda_A=\lambda_0+(A*\Delta\lambda)$, where $A=\{0, 1, \ldots (N-1)\}$.

For illustrative purposes, the predetermined increment/decrement can have a value of 0.5 nm. To illustrate embodiments where the excitation wavelength is increased, when $\lambda_0$=670 nm, $\lambda_1$=670.5 nm, $\lambda_2$=671 nm, and so on according to the number of spectra to be detected (N). In some embodiments, the excitation wavelength is decreased by a decrement.

At step 940, the analyte can be illuminated using light having the increased or decreased wavelength. To illustrate embodiments where the excitation wavelength is increased, the light can have a wavelength $\lambda_1$=670.5 nm, $\lambda_2$=671 nm, or so on according to the number of spectra to be detected (N).

At step 950, a spectrum (e.g., including Raman scattering (or Raman signal) and fluorescence) can be detected from the illuminated analyte. In some embodiments, the light (having the increased/decreased excitation wavelength) hitting the analyte results in Raman scattering (or Raman signal) and fluorescence. For example, the Raman scattering and fluorescence can be detected by the Raman instrument (e.g., using detector 130 optionally through optional sampling apparatus 140A (FIG. 1)). The detected Raman scattering and fluorescence may appear (e.g., when graphed/plotted) as shown in graphical representation 700 (FIG. 7) (where the excitation wavelength is the increased/decreased excitation wavelength, for example, $\lambda_1$, $\lambda_2$, and so on according to the number of spectra to be detected). Each detected spectrum (e.g., data, graphical representation, and the like) can be stored by (and/or in) the Raman instrument and/or the computing system.

According to various embodiments, the spectrum can be detected at step 950 using a time-resolving technique described below in relation to FIG. 10.

At step 960, a determination is made as to whether another spectrum is to be detected. In some embodiments, the predetermined number of spectra to be detected (N) is compared to the number of spectra (actually) detected. When the predetermined number of spectra to be detected (N) is less than the number of spectra detected, method 900 can proceed to step 930. When the predetermined number of spectra to be detected (N) is equal to the number of spectra actually detected, method 900 can proceed to step 970. For example, when N=6 and spectra are already detected for $\lambda_0$, $\lambda_1$, $\lambda_2$, $\lambda_3$, $\lambda_4$, and $\lambda_5$, method 900 can proceed to step 970. By way of further non-limiting example, when N=3 the detected Raman scattering and fluorescence (e.g., detected for each of $\lambda_0$, $\lambda_1$, and $\lambda_2$) may appear (e.g., when graphed/plotted together) as shown in graphical representation 800 (FIG. 8).

Optionally at step 970, a Raman spectrum of the analyte can be recovered using the detected spectra (e.g., N detected spectra). In some embodiments, the Raman spectrum of the analyte can be recovered using expectation maximization techniques. The recovered Raman spectrum may appear (e.g., when graphed/plotted) as shown in graphical representation 700 (FIG. 7) (e.g., Raman signal 730 (730A-D) without fluorescence). Recovering the Raman spectrum of the analyte is described further below in relation to FIG. 11.

Optionally at step 980, a molecule can be identified using the recovered Raman spectrum. For example, a database of known Raman spectrum for certain molecules can be searched using (e.g., compared to) the recovered Raman spectrum to find a match.

Figure 10:
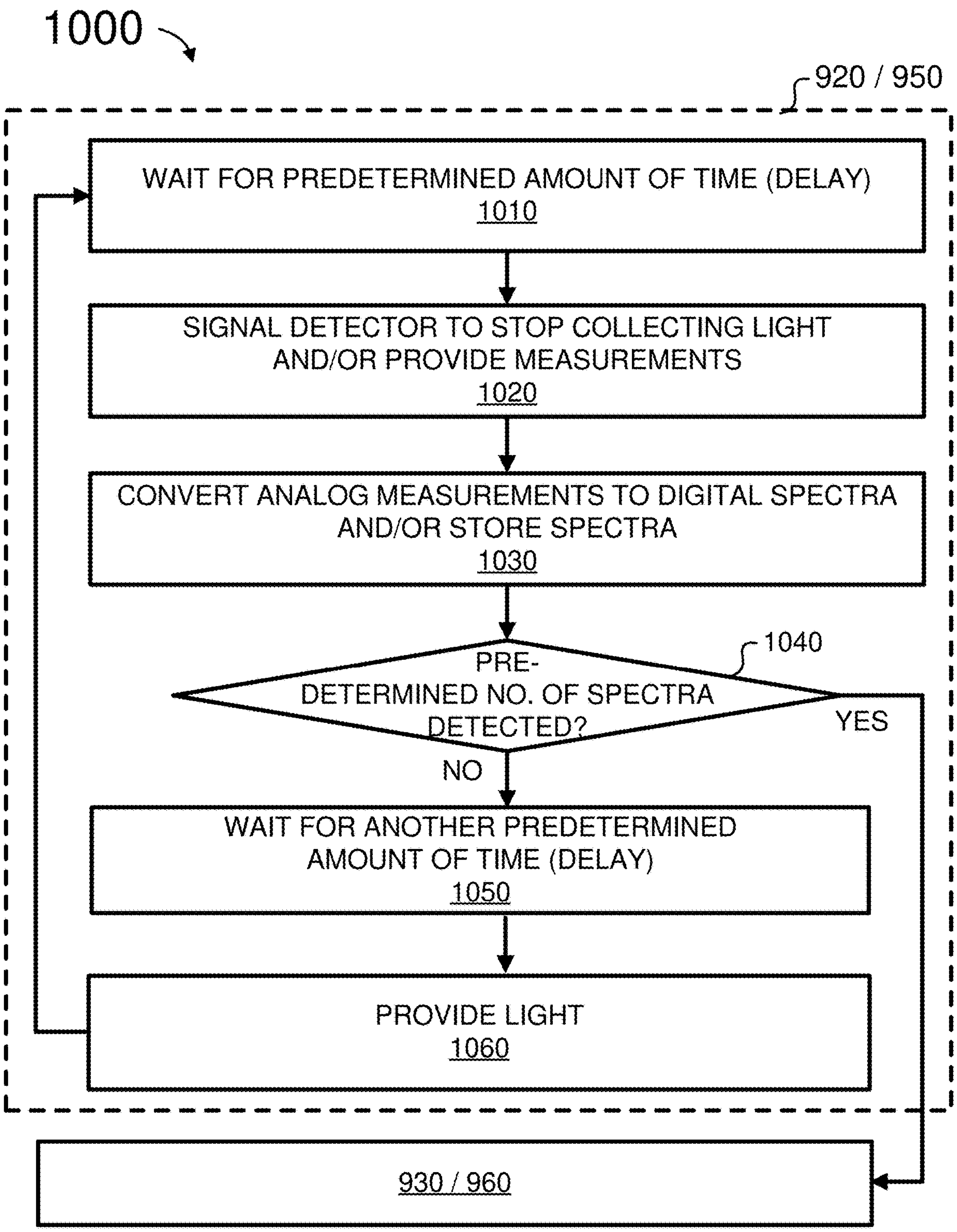
FIG. 10 is a simplified flow diagram of a method for time resolved spectroscopy, according to various embodiments.

FIG. 10 illustrates method 1000 for time-resolved spectroscopy, according to some embodiments. Method 1000 can be performed by a Raman instrument and/or a computing system. The Raman instrument can have at least some of the characteristics of Raman instrument 110A (FIG. 1), Raman instrument 110B (FIG. 2), and Raman instrument 110C (FIG. 3). The computing system can have at least some of the characteristics of computing system 240 (FIG. 2) and computing system 1300 (FIG. 13).

Steps 1010-1060, in whole or in part, provide further detail of step 920 and/or 950 in FIG. 9. Following step 910 and/or 940, method 1000 can commence at step 1010, where there is a wait or pause for a predetermined delay (e.g., after the analyte is illuminated). In some embodiments, the predetermined delay can be controlled by delay 180 in FIG. 1. For example, the predetermined delay can be substantially the duration of the gate (e.g., time window 630 in FIG. 6A), which can depend on the material to be measured. Additionally or alternatively, the predetermined delay can also take into account latency (delays) arising from detection of the light being provided (e.g., laser firing), detector 136A de-activating after receipt of the instruction or control signal, characteristics of the material, and the like. For example, the preceding example latencies in system 100 (FIG. 1) can be characterized and delay 180 calibrated to take into them account (or otherwise compensate for them).

At step 1020, the detector (e.g., detector 136A in FIG. 12) can be signaled to stop collecting returned light and/or provide measurements. In some embodiments, an instruction or control signal can be provided to the detector (e.g., detector 136A and/or a control circuit(s) for detector 136A), which de-activates the detector (e.g., detector 136A stops measuring light/photons, outputs the light measurements, and/or optionally resets detector 136A to detect further photons such as by quenching).

At step 1030, the provided (received) measurements can be (optionally) converted to a digital spectra (e.g., using an ADC) and/or the digital spectra can be stored. In some embodiments, when detector 136A is a SPAD array which provides a digital output, the measurements (e.g., spectra) from detector 136A are already digital spectra and do not need conversion, but can still be stored.

At step 1040, a determination is made as to whether another spectrum is to be detected. In some embodiments, the predetermined number of spectra to be detected (P) is compared to the number of spectra (actually) detected. For example, when the predetermined number of spectra to be detected (P) is less than the number of spectra detected, method 1000 can proceed to step 1050. When the predetermined number of spectra to be detected (P) is equal to the number of spectra actually detected, method 1000 can proceed to steps 930 (e.g., when method 1000 is performed at step 920 in FIG. 9) and/or 960 (e.g., when method 1000 is performed at step 950 in FIG. 9).

In some embodiments, steps 1010-1040 can be repeated in a range of 9-9,999,999 times (e.g., P=10-1,000,000,000). For example, P can be in a range of 1,000-10,000 times. By way of further non-limiting example, P can be 1,000,000 samples taken in 50 seconds at a sample rate (e.g., steps 1010-1040 are repeated) of 20 kHz. In 50 seconds, some measurable characteristics of the material to be measured (e.g., analyte 150A-C in FIGS. 1-3) do not appreciably change (e.g., an accurate reading can be performed). In some embodiments, there is latency (a delay) between when detector 136A receives an instruction or control signal to de-activate and when detector 136A actually de-activates. This latency can be, for example, 10 ps-1,000 ps. In some embodiments, this latency is on the order of 100 ps. For example, when detector 136A continues measuring after the end of the gate (e.g., time window 1170A in FIG. 11A, at time t2), detector 136A will measure at least some fluorescence.

In addition, detector 136A may detect ambient/background radiation. Ambient/background radiation can include one or more of: Ultraviolet C (UVC) light (e.g., 100 nm-280 nm wavelength), Ultraviolet B (UVB) light (e.g., 280 nm-315 nm wavelength), Ultraviolet A (UVA) light (e.g., 315 nm-400 nm wavelength), visible light (e.g., 380 nm-780 nm wavelength), and infrared (e.g., 700 nm-1 mm wavelength). To reduce the distortion (to the measured spectra) introduced by fluorescence and/or ambient/background radiation, multiple measurements can be taken, since the measured fluorescence and/or ambient/background radiation can vary across multiple measurements.

At step 1050, method 1000 can wait or pause for another predetermined delay before proceeding to step 1060. The another predetermined delay determines at least partially a frequency at which light is provided to (e.g., a laser fires at) the material and the returned light measured. The provided light (e.g., laser pulses) can be temporally spaced, such that at least the fluorescence from the material dies out (e.g., the end of the fluorescence lifetime is reached) before the next laser pulse is sent out. In other words, the time between laser pulses (e.g., the another predetermined delay) can be longer than the fluorescence lifetime/duration (e.g., FIG. 11B). Additionally or alternatively, the another predetermined delay can be selected such that when detector 136A is a SPAD array, each pixel in the SPAD array can be quenched (and ready to detect a photon) before light is provided again at step 1060.

In some embodiments, the frequency at which the light is provided (e.g., the laser fires) can be in the range of 1 KHz-100 KHz. For example, the frequency is on the order of tens of kilohertz, such as 20 KHz (e.g., the another predetermined delay (uncompensated) is 50 ms). The another predetermined delay can be adjusted to compensate for latency (delays) incurred by at least some of steps 1010-1050 (e.g., the time is takes to perform at least some of steps 1010-1050). The another predetermined delay can be different from the predetermined delay.

At step 1060, the analyte is illuminated. For example, step 1060 is a repeat of step 910 (e.g., when method 1000 is performed at step 920 in FIG. 9) and/or 940 (e.g., when method 1000 is performed at step 950 in FIG. 9).

According to various embodiments, steps 1010-1060 can be applied (one or more times) to optical phantoms, each optical phantom having/mimicking a different concentration of a particular molecule (FIG. 9). To perform a calibration, instead of step 930 and/or 960, a (Raman) spectrum or spectrograph (e.g., intensity at one or more wavelengths) of the material can be recovered using the detected spectra (e.g., P detected spectra). In some embodiments, the (Raman) spectrum or spectrograph (e.g., intensity at one or more wavelengths) of the material can be recovered by summing the detected spectra. Since the measured fluorescence and noise introduced by ambient light can vary across multiple measurements, summing multiple measurements can reduce/eliminate distortions introduced by fluorescence and/or ambient light. Additionally or alternatively, statistical methods (e.g., arithmetic mean, rolling average, and the like) can be used to recover the (Raman) spectrum or spectrograph.

The recovered (Raman) spectrum or spectrograph may appear (e.g., when graphed/plotted) as shown in graphical representation 700 (FIG. 7) (e.g., Raman signal 730 (730A-D) substantially without fluorescence). A molecule (and optionally a concentration of the molecule) can be identified using the recovered (Raman) spectrum. In some embodiments, the recovered (Raman) spectrum or spectrograph (e.g., intensity at one or more wavelengths) can be calibrated using one or more optical phantoms. For example, steps 1010-1060 can be applied to an optical phantom which mimics the material to be tested. In the case of biological analytes, optical phantoms are tissue-simulating objects used to mimic light propagation in living tissue. Optical phantoms can be designed with absorption and scattering properties matching optical characteristics of living human and animal tissues.

During calibration, the resulting recovered spectrum from each phantom/concentration can be correlated with the molecule (and concentration) of that optical phantom. Using calibration, the correlation between the recovered (Raman) spectrum or spectrograph (e.g., intensity at one or more wavelengths) of the material to be measured and the presence/concentration of a certain molecule can be established. In some embodiments, the spectra generated during the calibration process are stored in a database and the actual spectrum produced when taking real measurements can be compared to the stored spectra. The characteristics of a matching stored spectrum can be associated with the actual spectrum.

Additionally, calibration using optical phantoms for other molecules at different concentrations can be performed. Although a calibration process for detecting a range of concentrations is described, calibration can be performed for detecting the presence of a molecule (e.g., using a phantom having a minimum, threshold, or maximum concentration of the molecule).

Figure 11:
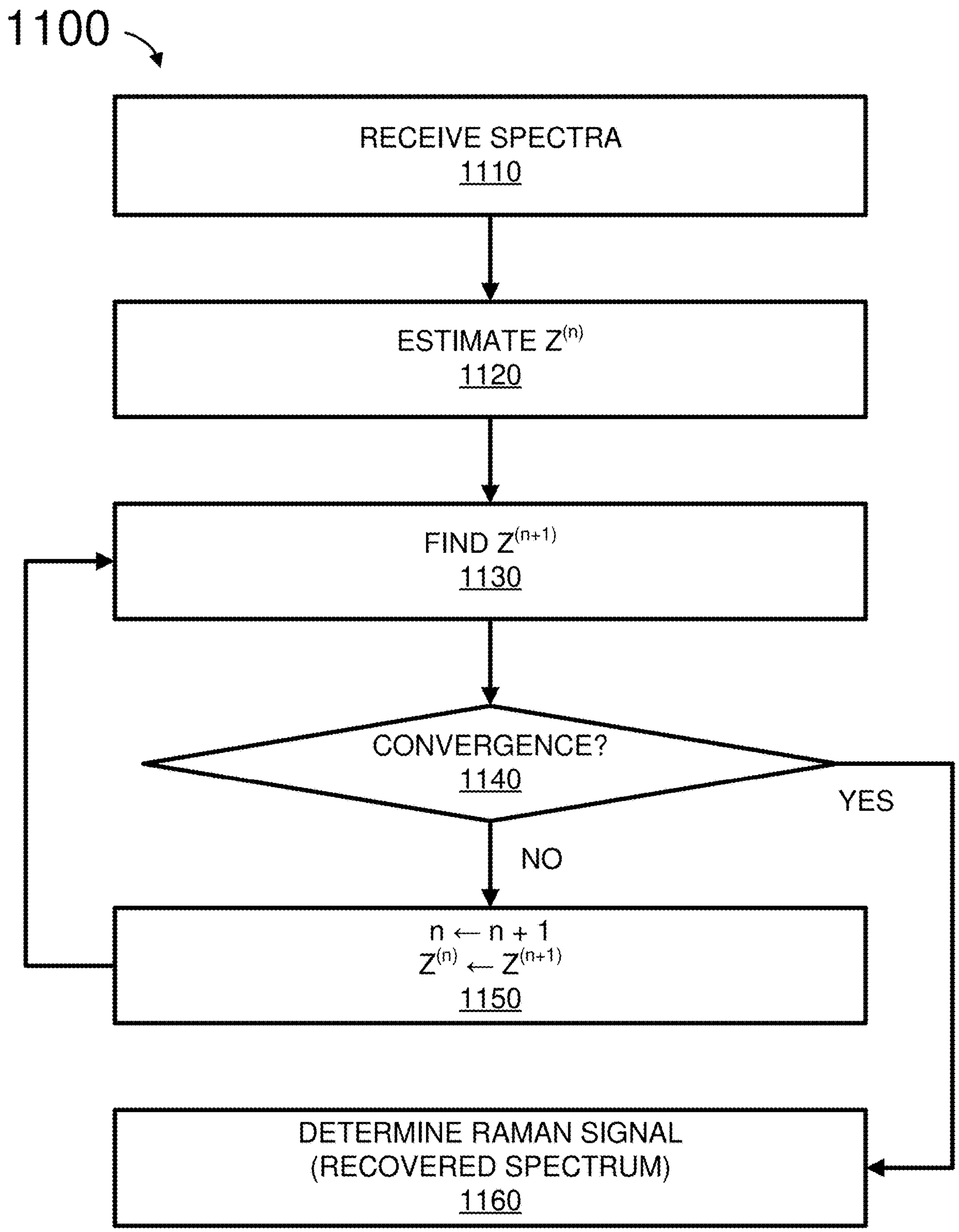
FIG. 11 is a simplified flow diagram of a method for recovering a Raman spectrum, in accordance with some embodiments.

FIG. 11 shows method 1100 for recovering a Raman spectrum of an analyte using expectation maximization techniques and the detected spectra, according to some embodiments. Method 1100 can commence at Step 1110, where the detected spectra (e.g., N detected spectra from method 900 in FIG. 9) can be received. By way of non-limiting example, the detected spectra are referred to as vector X. The detected intensity in vector X includes the intensity of fluorescence and the Raman signal (e.g., I=IR+IF). According to some embodiments, vector X (e.g., detected spectra) can be represented by:

$$X = \begin{bmatrix} Y_{1,1} \\ Y_{1,2} \\ \vdots \\ Y_{1,N} \\ Y_{2,1} \\ Y_{2,2} \\ \vdots \\ Y_{2,N} \\ \vdots \\ Y_{K-1,N} \\ Y_{K,1} \\ Y_{K,2} \\ \vdots \\ Y_{K,N} \end{bmatrix} \quad (1)$$

where each $Y_i$ (where i={1, 2, ... K}) is a measured spectra using a different excitation wavelength.

By way of further non-limiting example, the (separate) values of the fluorescence and the Raman signal are referred to as vector Z. Vector Z (e.g., (separate) values of the fluorescence and the Raman signal) can be represented by a vector have 2N dimensions:

$$Z = \begin{bmatrix} S_1^F \\ S_2^F \\ \vdots \\ S_N^F \\ S_1^R \\ S_2^R \\ \vdots \\ S_N^R \end{bmatrix} \quad (2)$$

where the fluorescence spectrum is $S^F$ and the Raman spectrum is $S^R$.

A relationship between vector X and vector Z can be represented as a matrix of (predetermined) parameters, matrix H. By way of non-limiting example, a relationship between vector X, vector Z, and matrix H can be:

$$H \times Z = X \quad (3)$$

where matrix H can be represented by a KN×2N matrix having predetermined values, such as:

$$H = \begin{bmatrix} 1, 0, 0, \ldots, 0 \\ 0, 1, 0, \ldots, 0 \\ \vdots \\ 0, 0, 0, \ldots, 1 \\ 0, 0, 0, \ldots, 0 \\ 1, 0, 0, \ldots, 0 \\ 0, 1, 0, \ldots, 0 \\ \vdots \\ 0, 0, 0, \ldots, 1 \end{bmatrix} \quad (4)$$

The relationship depicted in equation 3 is an inverse problem: using a known vector X to determine vector Z, where matrix H is a large matrix which cannot be inverted. In various embodiments, the inverse problem in equation 3 is solved using Maximum Likelihood-Expectation Maximization (ML-EM) iterative methods included in methods discussed herein. For example, among all possible values for vector Z, one that maximizes the probability of producing vector X is selected. The maximization can be performed using the Expectation Maximization (EM) techniques included in method 1100.

At step 1120, an initial guess vector $Z^{(n=0)}$ can be used for vector Z (e.g., $S^F$ and $S^R$). In some embodiments, vector $Z^{(n=0)}$ can be arbitrary, a prior calculated estimate of vector Z (e.g., using method 1100), combinations thereof, and the like.

At step 1130, an estimate for vector Z (e.g., $Z^{(n+1)}$) can be determined. For example, Z can be estimated using:

$$z_i^{(n+1)} = z_i^n * \left( \frac{1}{\sum_j H_{ji}} \right) * \left( \sum_j H_{ji} \right) * \left( \frac{X_j}{\sum_k H_{jk} Z_k^n} \right) \quad (5)$$

At step 1140, the estimate for vector Z (e.g., vector $Z^{(n+1)}$) can be evaluated. In some embodiments, the estimate for vector Z is evaluated for convergence. For example, when a change between successive iterations (e.g., between vector $Z^n$ and vector $Z^{n+k}$, where k can be a number in the range of 0-10,000) is smaller than a predetermined amount (e.g., tolerance, such as 1%-10% change), then vector Z can be said to converge. The change can be determined between an iteration early in the method (e.g., vector $Z_j$ (where j can be a number in the range of 5-10,000) and a latest iteration. Additionally or alternatively, vector Z can be said to have converged after a predetermined number (e.g., 10-50,000) of iterations. In various embodiments, for some spectra having different fluorescence levels, changes in the estimate for vector Z are negligible (e.g., smaller than a predetermined amount) after around 2,000 iterations (e.g., 1,000-3,000 iterations). When vector Z has not converged or immediately after the first iteration (e.g., using vector $Z^{(n=0)}$), method 1100 can proceed to step 1150. When vector Z is determined to have converged, method 1100 can proceed to step 1160.

At step 1150, n can be incremented (e.g., n←n+1), Z can be incremented (e.g., $Z^{(n)} \leftarrow Z^{(n-1)}$) and method 1100 can perform another iteration by proceeding to step 830.

At step 1160, a next estimate for vector Z can be determined using vector X, matrix H, and the estimate for vector Z calculated in the prior iteration.

In various embodiments, method 1100 can be performed multiple times, each repetition using a different initial guess $Z^{(n=0)}$. For example, the initial guesses can be various combinations and permutations of arbitrary, prior calculated estimate of Z (e.g., using method 1100), and the like. A vector Z can be selected from among the repetitions of method 1100.

FIG. 12 depicts a table 1200 of example molecules 1210 which may be detected by the systems (e.g., system 100 (FIG. 1), system 200 (FIG. 2), and system) 300 (FIG. 3)), and detected using methods (e.g., method 900 (FIG. 9) and method 1000 (FIG. 10)) described herein. Conditions 1220 associated with each molecule 1210 are shown for illustrative purposes.

FIG. 13 illustrates an exemplary computer system 1300 that may be used to implement some embodiments of the present invention. The computer system 1300 in FIG. 13 may be implemented in the contexts of the likes of computing systems, networks, servers, or combinations thereof. The computer system 1300 in FIG. 13 includes one or more processor unit(s) 1310 and main memory 1320. Main memory 1320 stores, in part, instructions and data for execution by processor unit(s) 1310. Main memory 1320 stores the executable code when in operation, in this example. The computer system 1300 in FIG. 13 further includes a mass data storage 1330, portable storage device 1340, output devices 1350, user input devices 1360, a graphics display system 1370, and peripheral device(s) 1380.

The components shown in FIG. 13 are depicted as being connected via a single bus 1390. The components may be connected through one or more data transport means. Processor unit(s) 1310 and main memory 1320 are connected via a local microprocessor bus, and the mass data storage 1330, peripheral device(s) 1380, portable storage device 1340, and graphics display system 1370 are connected via one or more input/output (I/O) buses.

Mass data storage 1330, which can be implemented with a magnetic disk drive, solid state drive, or an optical disk drive, is a non-volatile storage device for storing data and instructions for use by processor unit(s) 1310. Mass data storage 1330 stores the system software for implementing embodiments of the present disclosure for purposes of loading that software into main memory 1320.

Portable storage device 1340 operates in conjunction with a portable non-volatile storage medium, such as a flash drive, floppy disk, compact disk, digital video disc, or Universal Serial Bus (USB) storage device, to input and output data and code to and from the computer system 1300 in FIG. 13. The system software for implementing embodiments of the present disclosure is stored on such a portable medium and input to the computer system 1300 via the portable storage device 1340.

User input devices 1360 can provide a portion of a user interface. User input devices 1360 may include one or more microphones, an alphanumeric keypad, such as a keyboard, for inputting alphanumeric and other information, or a pointing device, such as a mouse, a trackball, stylus, or cursor direction keys. User input devices 1360 can also include a touchscreen. Additionally, the computer system 1300 as shown in FIG. 13 includes output devices 1350. Suitable output devices 1350 include speakers, printers, network interfaces, and monitors.

Graphics display system 1370 include a liquid crystal display (LCD) or other suitable display device. Graphics display system 1370 is configurable to receive textual and graphical information and processes the information for output to the display device.

Peripheral device(s) 1380 may include any type of computer support device to add additional functionality to the computer system.

The components provided in the computer system 1300 in FIG. 13 are those typically found in computer systems that may be suitable for use with embodiments of the present disclosure and are intended to represent a broad category of such computer components that are well known in the art. Thus, the computer system 1300 in FIG. 13 can be a personal computer (PC), hand held computer system, telephone, mobile computer system, workstation, tablet, phablet, mobile phone, server, minicomputer, mainframe computer, wearable, or any other computer system. The computer may also include different bus configurations, networked platforms, multi-processor platforms, and the like. Various operating systems may be used including UNIX, LINUX, WINDOWS, MAC OS, PALM OS, QNX, ANDROID, IOS, CHROME, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the technology. Those skilled in the art are familiar with instructions, processor(s), and storage media.

In some embodiments, the computer system 1300 may be implemented as a cloud-based computing environment, such as a virtual machine operating within a computing cloud. In other embodiments, the computer system 1300 may itself include a cloud-based computing environment, where the functionalities of the computer system 1300 are executed in a distributed fashion. Thus, the computer system 1300, when configured as a computing cloud, may include pluralities of computing devices in various forms, as will be described in greater detail below.

In general, a cloud-based computing environment is a resource that typically combines the computational power of a large grouping of processors (such as within web servers) and/or that combines the storage capacity of a large grouping of computer memories or storage devices. Systems that provide cloud-based resources may be utilized exclusively by their owners or such systems may be accessible to outside users who deploy applications within the computing infrastructure to obtain the benefit of large computational or storage resources.

The cloud is formed, for example, by a network of web servers that comprise a plurality of computing devices, such as the computing system 600, with each server (or at least a plurality thereof) providing processor and/or storage resources. These servers manage workloads provided by multiple users (e.g., cloud resource customers or other users). Typically, each user places workload demands upon the cloud that vary in real-time, sometimes dramatically. The nature and extent of these variations typically depends on the type of business associated with the user.

It is noteworthy that any hardware platform suitable for performing the processing described herein is suitable for use with the technology. The terms "computer-readable storage medium" and "computer-readable storage media" as used herein refer to any medium or media that participate in providing instructions to a CPU for execution. Such media can take many forms, including, but not limited to, non-volatile media, volatile media and transmission media. Non-volatile media include, for example, optical, magnetic, and solid-state disks, such as a fixed disk. Volatile media include dynamic memory, such as system random-access memory (RAM).

Transmission media include coaxial cables, copper wire and fiber optics, among others, including the wires that comprise one embodiment of a bus. Transmission media can also take the form of acoustic or light waves, such as those generated during radio frequency (RF) and infrared (IR) data communications. Common forms of computer-readable media include, for example, a floppy disk, a flexible disk, a hard disk, magnetic tape, any other magnetic medium, a CD-ROM disk, digital video disk (DVD), any other optical medium, any other physical medium with patterns of marks or holes, a RAM, a programmable read-only memory (PROM), an erasable programmable read-only memory (EPROM), an electrically erasable programmable read-only memory (EEPROM), a Flash memory, any other memory chip or data exchange adapter, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

Computer program code for carrying out operations for aspects of the present technology may be written in any combination of one or more programming languages, including an object oriented programming language such as JAVA, SMALLTALK, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of wired and/or wireless network, including a (wireless) local area network (LAN/WLAN) or a (wireless) wide area network (WAN/WWAN), or the connection may be made to an external computer (for example, through the Internet using an Internet Service Provider, wireless Internet provider, and the like).

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

Aspects of the present technology are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated. The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

Aspects of the present technology are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

What is claimed is:

1. A method for hybrid time-resolved and time-shifted spectroscopy for measuring biological analytes, the method comprising:

illuminating an analyte using a first light from an excitation source, the first light having a first excitation wavelength;

detecting a first spectrum from the analyte illuminated by the first light using a time-resolved spectroscopy technique, the first spectrum including a first Raman signal and fluorescence;

illuminating the analyte using a second light from the excitation source, the second light having a second excitation wavelength, the second excitation wavelength being larger than the first excitation wavelength by a first predetermined increment;

detecting a second spectrum from the analyte illuminated by the second light using a time-resolved spectroscopy technique, the second spectrum including a second Raman signal and the fluorescence, the detecting using a Raman spectrometer, the second Raman signal being shifted from the first Raman signal by a second predetermined increment;

illuminating the analyte using a third light from the excitation source, the third light having a third excitation wavelength, the third excitation wavelength being larger than the second excitation wavelength by the first predetermined increment;

detecting a third spectrum from the analyte illuminated by the third light using a time-resolved spectroscopy technique, the third spectrum including a third Raman signal and the fluorescence, the third Raman signal being shifted from the second Raman signal by the second predetermined increment;

recovering the first Raman signal using the first spectrum, the second spectrum, and the third spectrum using an inverse transform; and using the first Raman signal to identify and measure at least one molecule of the analyte using a database of identified Raman signals.

2. The method of claim 1, wherein the time-resolved spectroscopy technique comprises:

receiving, by a detector, scattered light from the analyte responsive to the illuminating an analyte using a respective one of the first light, second light, and third light; and signaling the detector, after a delay commencing after providing the respective one of the first light, second light, and third light, to provide a respective one of the first spectrum, second spectrum, and third spectrum of the received scattered light, the delay being a predetermined amount of time beginning when the excitation source emits light.

3. The method of claim 1, wherein the first excitation wavelength, the second excitation wavelength, and the third excitation wavelength are each within a range from ultraviolet light to near infrared light.

4. The method of claim 3, wherein the first excitation wavelength, the second excitation wavelength, and the third excitation wavelength are each within a range from 650 nm to 950 nm.

5. The method of claim 1, wherein the first light, the second light, and the third light are provided by a monochromatic light source.

6. The method of claim 5, wherein the monochromatic light source is a tunable laser.

7. The method of claim 1, wherein the analyte is at least one of living plant and animal tissue.

8. The method of claim 1, wherein the analyte is a living human limb.

9. The method of claim 1, wherein the at least one molecule is one or more of blood sugar, cholesterol, and a cancer biomarker.

10. The method of claim 1, wherein the recovering includes iteratively applying expectation maximization techniques.

11. A system for hybrid time-resolved and time-shifted spectroscopy for measuring biological analytes, the system comprising:

a processor; and a memory communicatively coupled to the processor, the memory storing instructions executable by the processor to perform a method comprising:

illuminating an analyte using a first light from an excitation source, the first light having a first excitation wavelength;

detecting a first spectrum from the analyte illuminated by the first light using a time-resolved spectroscopy technique, the first spectrum including a first Raman signal and fluorescence;

illuminating the analyte using a second light from the excitation source, the second light having a second excitation wavelength, the second excitation wavelength being larger than the first excitation wavelength by a first predetermined increment;

detecting a second spectrum from the analyte illuminated by the second light using a time-resolved spectroscopy technique, the second spectrum including a second Raman signal and the fluorescence, the detecting using a Raman spectrometer, the second Raman signal being shifted from the first Raman signal by a second predetermined increment;

illuminating the analyte using a third light from the excitation source, the third light having a third excitation wavelength, the third excitation wavelength being larger than the second excitation wavelength by the first predetermined increment;

detecting a third spectrum from the analyte illuminated by the third light using a time-resolved spectroscopy technique, the third spectrum including a third Raman signal and the fluorescence, the third Raman signal being shifted from the second Raman signal by the second predetermined increment;

recovering the first Raman signal using the first spectrum, the second spectrum, and the third spectrum using an inverse transform; and using the first Raman signal to identify and measure at least one molecule of the analyte using a database of identified Raman signals.

12. The system of claim 11, wherein the first excitation wavelength, the second excitation wavelength, and the third excitation wavelength are each within a range from ultraviolet light to near infrared light.

13. The system of claim 12, wherein the first excitation wavelength, the second excitation wavelength, and the third excitation wavelength are each within a range from 650 nm to 950 nm.

14. The system of claim 11, wherein the monochromatic light source is a tunable laser.

15. The system of claim 11, wherein illuminating the analyte using the first light includes illuminating at least one of living plant and animal tissue.

16. The system of claim 11, wherein illuminating the analyte using the first light includes illuminating a living human limb.

17. The system of claim 11, wherein the at least one molecule is one or more of blood sugar, cholesterol, and a cancer biomarker.

18. The system of claim 11, wherein the recovering includes iteratively applying expectation maximization techniques.

19. A system for non-invasive measurement of biological analytes comprising:

means for illuminating an analyte using a plurality of lights, the plurality of lights including a first light, a second light and a third light, the first light having a first excitation wavelength, the second light having a second excitation wavelength, the second excitation wavelength being larger than the first excitation wavelength by a first predetermined increment, the third light having a third excitation wavelength, the third excitation wavelength being larger than the second excitation wavelength by the first predetermined increment;

means for detecting a first spectrum from the analyte illuminated by the first light using a time-resolved spectroscopy technique, the first spectrum including a first Raman signal and fluorescence;

means for detecting a second spectrum from the analyte illuminated by the second light using a time-resolved spectroscopy technique, the second spectrum including a second Raman signal and the fluorescence, the detecting using a Raman spectrometer, the second Raman signal being shifted from the first Raman signal by a second predetermined increment;

means for detecting a third spectrum from the analyte illuminated by the third light using a time-resolved spectroscopy technique, the third spectrum including a third Raman signal and the fluorescence, the third Raman signal being shifted from the second Raman signal by the second predetermined increment;

means for recovering the first Raman signal using the first spectrum, the second spectrum, and the third spectrum using an inverse transform; and means for using the first Raman signal to identify and measure at least one molecule of the analyte using a database of identified Raman signals.

* * * * *